United States Patent [19]

Sugihara et al.

[11] 4,284,644
[45] Aug. 18, 1981

[54] SPIROBENZOFURANONE COMPOUNDS

[75] Inventors: Hirosada Sugihara, Osaka; Masazumi Watanabe, Kawanishi; Mitsuru Kawada, Amagasaki; Isuke Imada, Osaka, all of Japan

[73] Assignee: Takeda Chemical Industries, Ltd., Osaka, Japan

[21] Appl. No.: 115,548

[22] Filed: Jan. 25, 1980

Related U.S. Application Data

[63] Continuation-in-part of Ser. No. 968,520, Dec. 11, 1978, abandoned.

[30] Foreign Application Priority Data

| Dec. 27, 1977 | [JP] | Japan | 52-159177 |
| Jun. 19, 1978 | [JP] | Japan | 53-74700 |
| Nov. 6, 1978 | [JP] | Japan | 53-136967 |
| May 4, 1979 | [JP] | Japan | 54-55082 |
| Jun. 25, 1979 | [JP] | Japan | 54-80551 |

[51] Int. Cl.³ .................................. A61K 31/34
[52] U.S. Cl. .................. 424/285; 424/248.57; 424/250; 424/267; 424/274; 260/326.34; 260/326.36; 260/326.5 S; 260/326.5 CA; 260/326.5 SF; 260/346.22; 260/346.71; 260/346.73; 544/153; 544/376; 546/196
[58] Field of Search ............... 260/346.22, 346.71, 260/346.73, 326.34, 326.36, 326.5 S, 326.5 SF, 326.5 CA; 544/153, 376; 546/196; 424/248.57, 267, 274, 250, 285

[56] References Cited

U.S. PATENT DOCUMENTS 4,105,670  8/1978  Noguchi et al. ............ 260/326.11 R

OTHER PUBLICATIONS

Okitsu et al., Heterocycles, vol. 6, No. 11 (1977), pp. 1877-1879.
Donnelly et al., Chem. and Industry (1967), pp. 1402-1403.

*Primary Examiner*—Henry R. Jiles
*Assistant Examiner*—Bernard Dentz
*Attorney, Agent, or Firm*—Stevens, Davis, Miller & Mosher

[57]  ABSTRACT

Novel spiro compounds of the formula:

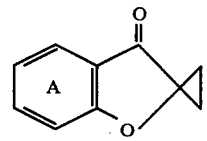

wherein Ring A represents a benzene ring or a naphthalene ring, said rings being unsubstituted or substituted by at least one of lower alkyl, nitro, halogen, amino which may optionally be substituted, hydroxyl which may optionally be substituted, acyl, sulfamoyl, carboxyl, lower alkoxycarbonyl, carbamoyl which may optionally be substituted, ureido which may optionally be substituted, thioureido which may optionally be substituted, lower alkylthio, lower alkylsulfinyl, lower alkylsulfonyl, aminomethyl which may optionally be substituted, cyano and phenyl, have gastric secretion inhibitive, anti-inflammatory and analgesic activities, and are of value as drugs.

30 Claims, No Drawings

SPIROBENZOFURANONE COMPOUNDS

This application is a continuation-in-part of Ser. No. 968,520, filed Dec. 11, 1978 now abandoned.

This invention relates to spiro compounds and use of said compounds.

The present spiro compounds have the following formula:

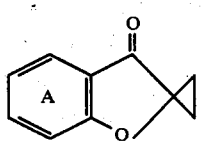
(I)

wherein Ring A represents a benzene ring or a naphthalene ring, said rings being unsubstituted or substituted by at least one of lower alkyl, nitro, halogen, amino which may optionally be substituted, hydroxyl which may optionally be substituted, acyl, sulfamoyl, carboxyl, lower alkoxycarbonyl, carbamoyl which may optionally be substituted, ureido which may optionally be substituted, thiouredio which may optionally be substituted, lower alkylthio, lower alkylsulfinyl, lower alkylsulfonyl, aminomethyl which may optionally be substituted, cyano and phenyl.

A preferred embodiment privides compounds of the formula:

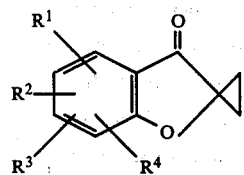
(I')

wherein
each of $R^1$, $R^2$, $R^3$ and $R^4$ is independently hydrogen, $C_{1-6}$ alkyl, nitro, halogen, hydroxyl, $C_{1-6}$ alkoxy, mono- or di-$C_{1-4}$ alkylamino-$C_{1-6}$ alkoxy, phenyl-$C_{1-4}$ alkyloxy, $C_{2-6}$ alkanoyloxy, benzoyloxy, $C_{2-6}$ alkanoyl, benzoyl, sulfamoyl, carboxyl, $C_{2-6}$ alkoxycarbonyl, carbamoyl, $C_{1-4}$ alkylcarbamoyl, di-$C_{1-4}$ alkylamino-$C_{1-4}$ alkylcarbamoyl, N-$C_{1-4}$ alkylpyrrolidinyl-$C_{1-4}$ alkylcarbamoyl, ureido, $C_{1-4}$ alkylureido, thioureido, $C_{1-4}$ alkylthioureido, $C_{1-4}$ alkylthio, $C_{1-4}$ alkylsulfinyl, $C_{1-4}$ alkylsulfonyl, aminomethyl, mono-or di-$C_{1-4}$ alkylaminomethyl, cyano, phenyl, amino, mono- or bis-($\beta$-hydroxyethyl)amino, $C_{1-4}$ alkylamino, di-$C_{1-4}$ alkylamino, $C_{2-4}$ alkanoylamino, $C_{1-4}$ alkanesulfonylamino, 1-pyrrolidinyl, piperidino, a 1-piperazinyl group, or morpholino, said 1-piperazinyl group being unsubstituted or substituted at the nitrogen atom of its 4-position by $C_{1-4}$ alkyl, phenyl-$C_{1-4}$ alkyl or $C_{2-4}$ alkanoyl, or two of $R^1$, $R^2$, $R^3$ and $R^4$ together form —CH=CH—CH=CH— at adjacent carbon atoms of the benzene ring.

Among the compounds of the formulas (I) and (I'), a preferred embodiment provides compounds the formula:

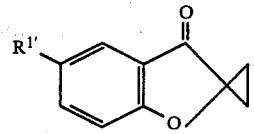
(I'')

wherein $R^{1'}$ is di-$C_{1-4}$ alkylamino, and pharmaceutically acceptable salts thereof, or formula:

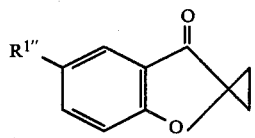
(I''')

wherein $R^{1''}$ is $C_{2-6}$ alkanoyl.

The substituents of Ring A including $R^1$, $R^2$, $R^3$, $R^4$, $R^{1'}$ and $R^{1''}$ in the above formulas (I), (I'), (I'') and (I''') are now explained in detail.

As examples of the lower alkyl group, there may be mentioned alkyl groups of 1 to 6 carbon atoms (e.g. methyl, ethyl, n-propyl, iso-propyl, n-butyl, iso-butyl, sec.-butyl, tert.-butyl, n-pentyl, iso-pentyl, n-hexyl, 2-methylpentyl, 2-ethylbutyl, etc.). The halogen may be chlorine, bromine, fluorine or iodine.

As examples of the amino group which may optionally be substituted, there may be mentioned amino, mono- or bis-($\beta$-hydroxyethyl)amino, mono- or dialkylamino, acylamino, sulfonylamino and cycloamino groups. The mono- or dialkylamino group may be an amino group mono- or di-substituted by alkyl groups of about 1 to 4 carbon atoms, such as methylamino, ethylamino, n-propylamino, iso-propylamino, n-butylamino, dimethylamino, diethylamino, di-n-propylamino, methylethylamino, etc. The acylamino group may for example be an alkanoylamino group containing about 2 to 4 carbon atoms (e.g. acetylamino, propionylamino, n-butyrylamino, iso-butyrylamino, etc.). The sulfonylamino group may for example be an alkanesulfonylamino group containing about 1 to 4 carbon atoms (e.g. methanesulfonylamino, ethanesulfonylamino, etc.). As the cycloamino group, there may be mentioned 5- or 6-membered cycloamino group which may contain N or O, for example, pyrrolidinyl, piperidino, piperazinyl or morpholino. The piperazinyl group may have a substituent, at the nitrogen atom of its 4-position, such as an alkyl group containing 1 to 4 carbon atoms (e.g. methyl, ethyl), a phenyl-$C_{1-4}$ alkyl group (e.g. benzyl) or an alkanoyl group containing 2 to 4 carbon atoms (e.g. acetyl, propionyl).

As examples of the hydroxyl group which may optionally be substituted, there may be mentioned hydroxyl, alkoxy, aralkyloxy or acyloxy. The alkoxy group preferably contains 1 to 6 carbon atoms (e.g. methoxy, ethoxy, n-propoxy, iso-propoxy, n-butoxy, iso-butoxy, sec.-butoxy, tert.-butoxy) and said alkoxy group may further be substituted, for example, by mono- or di-$C_{1-4}$ alkylamino groups (e.g. methylamino, ethylamino, dimethylamino, diethylamino). The aralkyloxy group may for example be phenyl-$C_{1-4}$ alkyloxy group (e.g. benzyloxy, phenethyloxy). The acyloxy group is preferably an alkanoyloxy group containing about 2 to 6 carbon atoms (e.g. acetyloxy, propionyloxy, n-butyryloxy, iso-butyryloxy), or benzoyloxy group, for instance.

The acyl group may for example be an alkanoyl group of about 2 to 6 carbon atoms (e.g. acetyl, propionyl, n-butyryl, iso-butyryl) or benzoyl.

The lower alkoxycarbonyl group may for example be an alkoxycarbonyl group of 2 to 6 carbon atoms (e.g. methoxycarbonyl, ethoxycarbonyl, n-propoxycarbonyl, iso-propoxycarbonyl, butoxycarbonyl).

As examples of the carbamoyl group which may optionally be substituted, there may be mentioned carbamoyl or $C_{1-4}$ alkylcarbamoyl (e.g. methylcarbamoyl, ethylcarbamoyl, n-propylcarbamoyl, iso-propylcarbamoyl), and said alkyl moiety of $C_{1-4}$ alkylcarbamoyl may further be substituted by di-$C_{1-4}$ alkylamino or N-$C_{1-4}$ alkylpyrrolidin-2-yl.

As examples of the ureido group which may optionally be substituted, there may be mentioned ureido or $C_{1-4}$ alkylureido (e.g. methylureido, ethylureido, n-propylureido, iso-propylureido).

As examples of the thioureido group which may optionally be substituted, there may be mentioned thioureido or $C_{1-4}$ alkylthioureido (e.g. methylthioureido, ethylthioureido, n-propylthioureido, iso-propylthioureido).

The lower alkyl moieties of the lower alkylthio, lower alkylsulfinyl and lower alkylsulfonyl groups may for example be $C_{1-4}$ alkyl (e.g. methyl, ethyl, n-propyl, iso-propyl).

As examples of the aminomethyl group which may optionally be substituted, there may be mentioned aminomethyl or mono- or di-$C_{1-4}$ alkylaminomethyl (e.g. methylaminomethyl, ethylaminomethyl, dimethylaminomethyl, diethylaminomethyl).

These substituents of the benzene ring, or naphthalene ring as the above-mentioned Ring A may be present, up to 4 at the maximum, in substitutable positions on the said ring, and may be the same or different. It is preferable that the benzene ring is substituted, at its 5-, 6- or 7-position (5-position is more desirable), by an amino group which may optionally be substituted (especially mono- or di-$C_{1-4}$ alkylamino group), or by an acyl group (especially $C_{2-4}$ alkanoyl group).

The spiro compound (I) of the present invention is produced by, for instance, decarboxylating a compound of the formula:

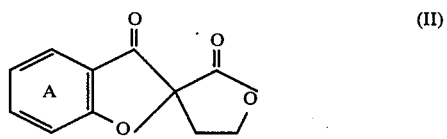

(II)

wherein Ring A is as defined hereinbefore.

This reaction is normally carried out in the presence of a catalyst which assists in decarboxylation. Among preferred catalysts for this purpose are metal halides (e.g. sodium chloride, sodium bromide, sodium iodide, potassium bromide, potassium chloride, potassium iodide, etc.) and quaternary ammonium salts (e.g. tetramethylammonium bromide, etc.). The reaction temperature is normally about 100° C. to 200° C. and preferably about 140° C. to 160° C., although the reaction may be conducted at higher or lower temperatures if it is desired to control the reaction velocity. Purging the reaction vessel with an inert gas (e.g. $N_2$, argon) is sometimes effective in preventing side reactions and improving yields. This reaction is normally carried out in a suitable solvent. While any solvent that will not interfere with the reaction may be employed, it is normally advantageous to employ a solvent having a boiling point higher than the reaction temperature (e.g. dimethyl sulfoxide, N,N-dimethylformamide, hexamethylphosphoramide).

Among the spiro compounds (I) of this invention, those having a substituent or substituents on Ring A can also be produced by subjecting a compound (I) wherein Ring A is unsubstituted, or a compound (I) having at least one hydrogen atom on its Ring A to a conventional alkylation, nitration, halogenation or acylation, depending on the desired substituents. An amino substituted compound (I) is produced by subjecting a correspondingly unsubstituted compound (I) to nitration followed by reduction, e.g., catalytic reduction. It is also possible to replace the substituents on Ring A of the compounds (I) with other substituents by a conventional reactions. Mono- or di-alkylamino substituted compounds (I) are produced, for example, by subjecting correspondingly amino-substituted compounds (I) to reductive alkylation, i.e., to reduction with a metal hydride such as sodium cyanoborohydride or catalytic reduction in the presence of a carbonyl compound (e.g. formaline, acetaldehyde, acetone), or to reaction with an alkyl halide to cause mono- or dialkylation. Mono- or dialkylamino substituted compounds (I) are alternatively produced by subjecting a correspondingly nitro-substituted compound (I) to catalytic reduction with a catalyst such as platinum oxide or Raney nickel in the presence of said carbonyl compound. This production may for example be illustrated in the following reaction scheme:

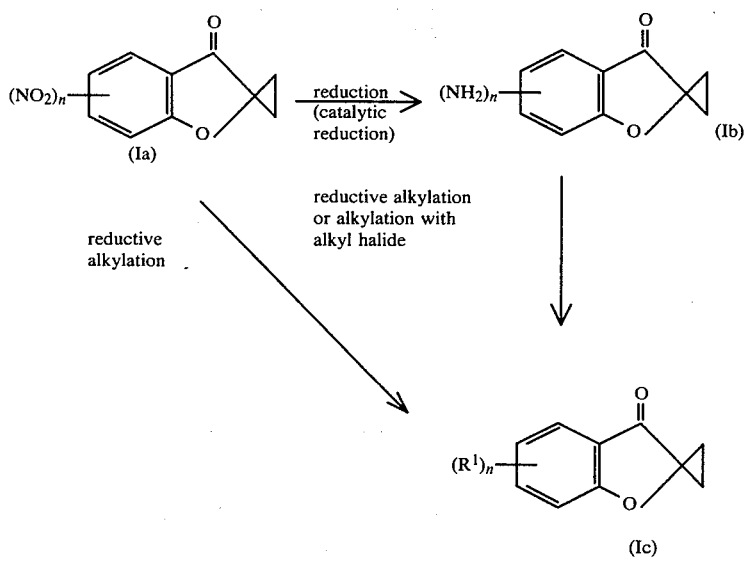

[wherein n is 1 or 2 and $R^1$ represents mono- or di-alkylamino as defined hereinbefore].

Compounds (I) having substituents on Ring A which are mono- or bis-($\beta$-hydroxyethyl)amino, can be produced by alkylation of the compounds (I) substituted by corresponding amino groups, with ethylene chlorohydrin or ethylene oxide.

Compounds (I), wherein the substituents on Ring A are carboxyl, are produced by subjecting an acetyl substituted compound (I) to a haloform reaction with hypohalogenites (e.g. sodium hypochlorite, sodium hypobromite), or by subjecting a pyridinium salt obtained from the acetyl substituted compound (I) with halogen (e.g. iodine) and pyridine to hydrolysis, or by subjecting to hydrolysis a cyano substituted compound (I). A compound (I) substituted on Ring A by alkoxycarbonyl, can be produced by subjecting a carboxyl substituted compound to esterification with alkyl halogenide or di-alkylsulfuric acid in the presence of alkali metal hydrogen carbonate (e.g. sodium hydrogen carbonate). A compound (I), substituted by carbamoyl or substituted carbamoyl, is produced by subjecting a cyano substituted compound (I) to hydrolysis with a base (e.g. sodium hydroxide, potassium hydroxide) in the presence of dimethylsulfoxide, or to a reaction with hydrogen peroxide under alkaline conditions, or by subjecting a carboxyl substituted compound (I) or reactive derivative thereof to condensation with amines. This condensation may be carried out by reacting the carboxyl substituted compound (I) with amines in the presence of a condensing agent (e.g. dicyclohexylcarbodiimide) and a suitable solvent (e.g. methylene chloride, pyridine, tetrahydrofuran). The reactive derivative of the carboxyl substituted compound (I) is, for example, an acid halide, active ester (e.g. alkyl ester, p-nitrophenyl ester), mixed acid anhydride obtained from the carboxy compound (I) or an alkyl chlorocarbonate (e.g. methyl chlorocarbonate, isobutyl chlorocarbonate). A compound (I), substituted on Ring A by ureido, substituted ureido, thioureido, or substituted thioureido, is produced by subjecting an amino substituted compound (I) to reaction with cyanic acid, isocyanic acid ester, thiocyanic acid or isothiocyanic acid ester. A cyano substituted compound (I) is produced by subjecting a diazonium salt derived from halo- or amino-substituted compound (I), to reaction with a metal cyanide (e.g. cuprous cyanide, sodium cyanide).

The contemplated compound (I) obtained in the foregoing manner can be isolated from the reaction mixture and purified by conventional procedures (e.g. distillation, recrystallization, column chromatography, etc.). According to the types of substituents on Ring A, the compound (I) may be isolated as pharmaceutically acceptable salts. For example, when an amino group (e.g. amino, mono- or di-alkylamino, mono- or bis($\beta$-hydroxyethyl)amino, aminoalkylcarbamoyl, pyrrolidinyl, morpholino, pyperazinyl) is present as the substituent, the compound (I) can be isolated as an acid addition salt (e.g. a mineral acid salt such as hydrochloride or hydrobromide, or an organic acid salt such as citrate tartrate, maleate, fumarate, or oxalate), or when the substituent is a carboxyl group or a hydroxyl group, the compound (I) can be isolated as an alkali metal salt (e.g. sodium salt, potassium salt, etc.). Said salts and optical isomers are included in the scope of the present invention.

The spiro compounds (I) according to this invention are new compounds which exhibit gastric secretion inhibitive, antiinflammatory, analgesic and other actions in mammalian animals (e.g. man, rat, mouse, guinea-pig, dog and pig), for instance, and are of value as antiulcer, antiinflammatory, analgesic and as drugs for the management of peptic ulcer, acute or chronic gastritis, lumbago, arthritis and other diseases. Management of a peptic ulcer in accordance with the present invention includes both the prophylactic administration of the spiro compounds (I) to prevent the outbreak of an ulcer in an ulcer prone patient, as well as the treatment of an existing peptic ulcer. In such medicinal applications, each compound (I) can be safely administered orally or parenterally, either as it is or as formulated with pharmaceutically acceptable carriers or diluents known per se into suitable dosage forms such as tablets, powders, capsules, injections and suppositories. While the recommended dosage depends on the subject, condition, route of administration, etc., the normal oral dosage for the treatment of peptic ulcer or acute or chronic gastritis is about 1 mg. to 20 mg. as compound (I) per kg body weight per dose, to be given once to 3 times daily.

The starting compound (II) which is employed in the practice of this invention can be prepared by the following route of synthesis or any process analogous thereto.

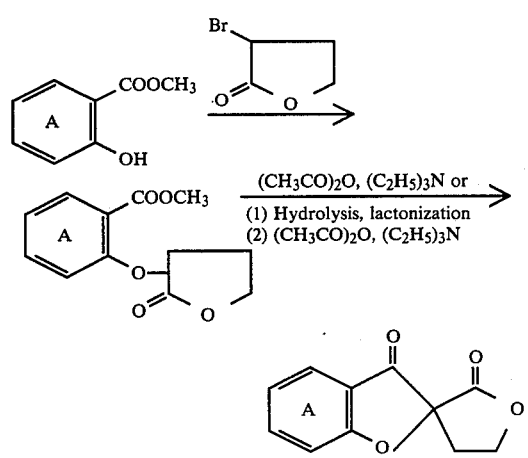

[wherein Ring A is as defined hereinbefore].

The following pharmacological test, and reference and working examples are given to describe this invention in further detail but should by no means be considered to be limiting the scope of this invention.

Pharmacological Test

The pharmacological activity of compound (I) of this invention was assayed by gastric-juice-secretion-inhibition test with rats, the results of which are as follows.

In accordance with the method described in "Gastroenterology" 5, 43(1945), inhibition of gastric-juice-secretion was evaluated by means of the pylorus ligated rats.

Five each of male Sprague-Dawley rats (each weighing 100–130 g.) were used for the control and five test groups. Each animal was deprived of food for 18 hours before the test, except drinking water. The pylorus of each animal was ligated under anesthetizing with ether, then the animals of test group were administered with each test compound at the dose of 50 mg./kg. intra duodenaly. Three hours after the ligation, the animals were sacrificed. Gastric secretions of the tested animals were collected and subjected to centrifuge for 10 minutes (3,500 r.p.m.), and the volume of gastric juice was measured. The result is as shown in the following table.

The ICR-type mice in groups of five animals were administered orally with these compounds at the dose of 500 mg./kg. to examine acute toxicity. No mouse was dead during 7 days in any groups.

Inhibition of Gastric-Juice Secretion in Rats

| Compound | Dose (i.d. mg/kg.) | Inhibition of Secretion (%) |
| --- | --- | --- |
| 5-Cl | 50 | 48 |
| 5-NO$_2$ | 50 | 57 |
| 5-N(CH$_3$)$_2$ | 50 | 78 |
| 4-Br, 5-NH$_2$ | 50 | 53 |
| 5-NHSO$_2$CH$_3$ | 50 | 68 |

REFERENCE EXAMPLE 1

To a mixture of 15.2 g. of methyl salicylate, 12 g. of sodium hydroxide and 150 ml. of N,N-dimethylformamide was added dropwise 25 g. of α-bromo-γ-butyrolactone under ice-cooling. The mixture was stirred at room temperature for 28 hours. The reaction mixture was made acidic by the addition of dilute hydrochloric acid and extracted with ethyl acetate. The extract was washed with water, dried and concentrated under reduced pressure. The residue was dissolved in 30 ml. of methanol, then 150 ml. of a 20% aqueous solution of sodium hydroxide was added dropwise and the solution was stirred at 55° C. for 30 minutes. The reaction mixture was made acidic with 60 ml. of concentrated hydrochloric acid, the resultant precipitate (salicylic acid) was filtered off and the filtrate was extracted with ethyl acetate. The extract was washed with water, dried and concentrated under reduced pressure.

The residue was dried in vacuo over phosphorus pentoxide for 24 hours, after which it was recrystallized from ethyl acetate-n-hexane (2:1). By the above procedure there was obtained 8.0 g of α-[(2-carboxyphenyl)oxy]-γ-butyrolactone as colorless needles melting at 113°–115° C. (Determined by Hot-Plate method, in all the examples hereinafter, the same method was applied to determination of melting points.).

Elemental analysis, for $C_{11}H_{10}O_5$: Calcd.: C, 59.46; H, 4.54. Found: C, 59.21; H, 4.51.

REFERENCE EXAMPLE 2

Using 18.7 g of methyl 5-chlorosalicylate, the procedure of Reference Example 1 was repeated to obtain 9.3 g of α-[(2-carboxy-4-chlorophenyl)oxy]-γ-butyrolactone as colorless needles melting at 159°–160.5° C.

Elemental analysis, for $C_{11}H_9ClO_5$: Calcd.: C, 51.48; H, 3.53; Cl, 13.82. Found: C, 51.22; H, 3.50; Cl, 13.70.

REFERENCE EXAMPLE 3

To a solution of 16.6 g of methyl 3-methylsalicylate in 200 ml of dimethylformamide was added 5.3 g of sodium hydride (50% suspension in Bayol 85).

Then, under ice-cooling, a solution of 18.2 g of α-bromo-γ-butyrolactone in 10 ml of dimethylformamide was added dropwise. The mixture was stirred at room temperature for 10 hours, after which time it was diluted with a small amount of water and distilled under reduced pressure to remove the solvent.

To the residue was added 60 ml of a 20% aqueous solution of sodium hydroxide and the mixture was stirred at 50°–60° C. for one hour. The reaction mixture was made acidic with 40 ml of concentrated hydrochloric acid and the precipitated crystals were collected by filtration to recover the unreacted 3-methylsalicylic acid. The filtrate was extracted with ethyl acetate, washed with water, dried and distilled under reduced pressure to remove the solvent. The residue was dried over phosphorus pentoxide at 50° C. for 12 hours, after which it was recrystallized from ethyl acetate-hexane. By the above procedure there was obtained 12 g of α-[(2-carboxy-6-methylphenyl)oxy]-γ-butyrolactone as colorless needles melting at 129°–131° C.

Elemental analysis, for $C_{12}H_{12}O_5$: Calcd.: C, 61.01; H, 5.12. Found: C, 61.00; H, 5.12.

REFERENCE EXAMPLE 4

Using 22 g of methyl 3,5-dichlorosalicylate, the reaction procedure of Reference Example 3 was repeated to obtain 14 g of α-[(2-carboxy-4,6-dichlorophenyl)oxy]-γ-butyrolactone as colorless crystals melting at 117°–120° C.

Elemental analysis, for $C_{11}H_8Cl_2O_5$: Calcd.: C, 45.38; H, 2.77. Found: C, 45.43; H, 2.66.

REFERENCE EXAMPLE 5

To a mixture of 32 g of methyl 5-benzyloxysalicylate, 17 g of anhydrous potassium carbonate and 500 ml of acetone was added 30.7 g of α-bromo-γ-butyrolactone under cooling with ice and, then, the mixture was refluxed for 15 hours. After cooling, the acetone was distilled off and 10% methanolic sodium hydroxide was added to the residue for hydrolysis. The reaction mixture was made acidic with hydrochloric acid and extracted with ethyl acetate. The extract was washed with water, dried over anhydrous sodium sulfate and distilled to remove the solvent. The residue was dissolved in dioxane (300 ml)-benzene (200 ml) and the solution was refluxed in the presence of p-toluenesulfonic acid (30 g), with the resultant water being continuously distilled off. The solvent was distilled off and the residue was diluted with water and extracted with ethyl acetate. The extract was washed with water, dried and concentrated to remove the solvent. The residue was recrystallized from ethyl acetate. By the above procedure there was obtained α-[(2-carboxy-4-benzyloxyphenyl)oxy]-γ-butyrolactone as colorless needles, m.p. 120°–122° C.

Yield 21.5 g.

Elemental analysis, for $C_{18}H_{16}O_6$: Calcd.: C, 65.85; H, 4.91. Found: C, 65.86; H, 4.96.

REFERENCE EXAMPLES 6–12

The following compounds were produced by procedure similar to that described in Reference Example 5.

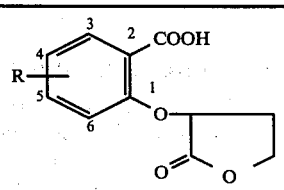

| Reference Example | Compound R | m.p. (°C.) | Molecular formula | Elemental Analysis (Upper rank: Calcd.) (Lower rank: Found) | |
|---|---|---|---|---|---|
| | | | | C | H |
| 6 | 5-OCH₃ | 130–133 | $C_{12}H_{12}O_6$ | 57.14 | 4.80 |
| | | | | 57.08 | 4.75 |
| 7 | 4-OCH₃ | 129–132 | $C_{12}H_{12}O_6$ | 57.14 | 4.80 |
| | | | | 57.04 | 4.78 |
| 8 | 4-COCH₃ | 155–158 | $C_{13}H_{12}O_6$ | 59.09 | 4.58 |

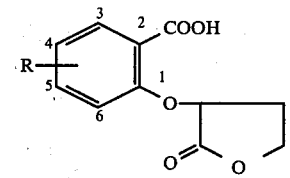

| Reference Example | Compound R | m.p. (°C.) | Molecular formula | Elemental Analysis (Upper rank: Calcd.) (Lower rank: Found) | |
|---|---|---|---|---|---|
| | | | | C | H |
| 9 | 3-OH | 189–198 (decomp.) | $C_{11}H_{10}O_6$ | 58.98 | 4.48 |
| | | | | 55.46 | 4.23 |
| | | | | 55.51 | 4.10 |
| 10 | 4,5- | 183–187 (decomp.) | $C_{15}H_{12}O_5$ | 66.17 | 4.44 |
| | | | | 66.06 | 4.22 |
| 11 | 4-C₆H₁₃ | 98–100 | $C_{17}H_{22}O_5$ | 66.65 | 7.24 |
| | | | | 66.50 | 7.28 |
| 12 | 5-CH(CH₃)₂ | 124–126 | $C_{14}H_{16}O_5$ | 63.62 | 6.10 |
| | | | | 63.60 | 6.18 |

REFERENCE EXAMPLE 13

51 g. of Methyl 4-acetylamino-5-chloro-2-hydroxybenzoate and 36.8 g. of anhydrous potassium carbonate were suspended in 350 ml. of N,N-dimethylformamide. To the suspension was added 55 g. of α-bromo-γ-butyrolactone, and the mixture was stirred at 60° C. for 12 hours. The solvent was evaporated off under reduced pressure. The residue was diluted with water and extracted with ethyl acetate. The extract was washed with water, dried and concentrated to remove the solvent. The residue was dissolved in chloroform, and subjected to column chromatography on silica gel, using chloroform as the eluent. The product was recrystallized from methanol. By the above procedure there was obtained α-[(5-acetylamino-4-chloro-2-methoxycarbonylphenyl)oxy]-γ-butyrolactone as pale yellow prisms, m.p. 118°–119° C.

Yield 32 g.

Elemental analysis, for $C_{14}H_{14}O_6NCl$: Calcd.: C, 51.31; H, 4.31; N, 4.27. Found: C, 51.24; H, 4.26; N, 4.16.

REFERENCE EXAMPLE 14

63 g. of Methyl 4-acetylamino-2-hydroxybenzoate was reacted in the same manner as in Reference Example 13. The product was subjected to column chromatography on silica gel and separated into two fractions. The crystals obtained from the first fraction were recrystallized from methanol to give 6-acetylamino-4',5'-dihydrospiro[benzo[b]furan]-2',3-dione as colorless plates, m.p. 220°–234° C.

Yield 1.4 g.

Elemental analysis, for $C_{13}H_{11}O_5N$: Calcd.: C, 59.77; H, 4.24; N, 5.36. Found: C, 59.71; H, 4.21; N, 5.28.

From the second fraction there was obtained α-[(5-acetylamino-2-methoxycarbonylphenyl)oxy]-γ-butyrolactone as a pale yellow oil. Yield 35 g. This only product can be subjected to the subsequent reaction step without further purification.

NMR(CDCl₃)δ: 2.10(3H, s, NCOCH₃), 2.65(2H, m, CH₂), 3.83(3H, s, COOCH₃), 4.45(2H, m, OCH₂), 4.98(1H, t, OCHCO), 7.09(1H, d, aromatic ring H), 7.66(1H, s, aromatic ring H), 7.73(1H, d, aromatic ring H).

REFERENCE EXAMPLE 15

24.4 g. of α-[(2-Carboxy-6-methylphenyl)oxy]-γ-butyrolactone was added to 120 ml. of fuming nitric acid at a temperature not higher than −40° C. The reaction solution was poured into ice water, and the precipitating crystals were collected by filtration, washed with water and dried. The crystals were recrystallized from methanol. By the above procedure there was obtained α-[(2-carboxy-6-methyl-4-nitrophenyl)oxy]-γ-butyrolactone as pale yellow prisms, m.p. 210° C.(decomp.). Yield 20.3 g.

Elemental analysis, for $C_{12}H_{11}O_7N$: Calcd.: C, 51.25; H, 3.94; N, 4.98. Found: C, 51.16; H, 3.93; N, 4.82.

REFERENCE EXAMPLE 16

3.04 g. of Methyl salicylate was reacted with α-bromo-γ-butyrolactone in the same manner as the corresponding step in Reference Example 13. The product was recrystallized from methanol to afford 3.3 g. of α-[(2-methoxycarbonylphenyl)oxy]-γ-butyrolactone as colorless needles melting at 62°–87° C.

Elemental analysis, for $C_{12}H_{12}O_5$: Calcd.: C, 61.01; H, 5.12. Found: C, 60.98; H, 4.99.

REFERENCE EXAMPLE 17

A mixture of 1.3 g. of α-[(2-carboxyphenyl)oxy]-γ-butyrolactone, 15 ml. of acetic anhydride and 3 ml. of triethylamine was stirred in nitrogen gas streams at 140° C. for 3.5 hours, at the end of which time the solvents were distilled off under reduced pressure. Column chromatography was carried out on the residue using 32.5 g. of silica gel and carbon tetrachloride-acetone (10:1). The fraction corresponding to the contemplated compound was taken, concentrated under reduced pressure and recrystallized from n-hexane-ethyl acetate(3:1). By the above procedure there was obtained 633 mg. of 4′,5′-dihydrospiro[benzo[b]furan-2(3H), 3′(2′H)-furan]-2′,3-dione as colorless needles melting at 111°–111.5° C.

Elemental analysis, for $C_{11}H_8O_4$: Calcd.: C, 64.70; H, 3.95. Found: C, 64.74; H, 3.70.

REFERENCE EXAMPLES 18–29

The following compounds were produced by procedure similar to that described in Reference Example 17.

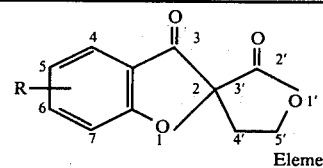

| Reference Example No. | Compound R | m.p. (°C.) | Molecular formula | Elemental analysis (Upper rank: Calcd.) (Lower rank: Found) C | H | N |
|---|---|---|---|---|---|---|
| 18 | 5-Cl | 132.5–133 | $C_{11}H_7ClO_4$ | 55.36 | 2.96 | |
|  |  |  |  | 55.49 | 2.79 | |
| 19 | 7-CH$_3$ | 103–104 | $C_{12}H_{10}O_4$ | 66.05 | 4.62 | |
|  |  |  |  | 66.31 | 4.63 | |
| 20 | 5-Cl, 7-Cl | 157–159 | $C_{11}H_6Cl_2O_4$ | 48.38 | 2.21 | |
|  |  |  |  | 48.47 | 2.14 | |
| 21 | 5-OCH$_2$Ph | 138–139 | $C_{18}H_{14}O_5$ | 69.67 | 4.55 | |
|  |  |  |  | 69.67 | 4.39 | |
| 22 | 6-OCH$_3$ | 106–108 | $C_{12}H_{10}O_5$ | 61.54 | 4.30 | |
|  |  |  |  | 61.62 | 4.22 | |
| 23 | 5-OCH$_3$ | 120–122 | $C_{12}H_{10}O_5$ | 61.54 | 4.30 | |
|  |  |  |  | 61.31 | 4.24 | |
| 24 | 5-COCH$_3$ | 132–134 | $C_{13}H_{10}O_5$ | 63.41 | 4.09 | |
|  |  |  |  | 63.57 | 4.02 | |
| 25 | 4-OCOCH$_3$ | 135–137 | $C_{13}H_{10}O_6$ | 59.54 | 3.84 | |
|  |  |  |  | 59.55 | 3.68 | |
| 26 | 5,6- (fused ring) | 168–170 | $C_{15}H_{10}O_4$ | 70.86 | 3.96 | |
|  |  |  |  | 70.83 | 3.63 | |
| 27 | 5-NO$_2$, 7-CH$_3$ | 127–130 | $C_{12}H_9O_6N$ | 54.76 | 3.45 | 5.32 |
|  |  |  |  | 55.00 | 3.24 | 5.36 |
| 28 | 5-C$_6$H$_{13}$ | oil | $C_{17}H_{20}O_4$ | 70.81 | 6.99 | |
|  |  |  |  | 71.14 | 6.99 | |
| 29 | 5-CH(CH$_3$)$_2$ | 71 | $C_{14}H_{14}O_4$ | 68.28 | 5.73 | |
|  |  |  |  | 68.39 | 5.67 | |

(Ph represents phenyl.)

REFERENCE EXAMPLE 30

A mixture of 23 g. of α-[(5-acetylamino-4-chloro-2-methoxycarbonylphenyl)oxy]-γ-butyrolactone, 46 ml. of triethylamine and 230 ml. of acetic anhydride was heated at 120° C. for 5 hours. The solvents were evaporated off under reduced pressure, then the residue was poured into ice-water. The precipitating crystals were collected by filtration, washed with water and dried, followed by recrystallization from ethyl acetate to give 6-diacetylamino-5-chloro-4′,5′-dihydrospiro[benzo[b]furan-2(3H), 3′(2′H)-furan]-2′,3-dione melting at 181°–185° C. Yield 6.8 g.

Elemental analysis, for $C_{15}H_{12}O_6NCl$: Calcd.: C, 53.34; H, 3.58; N, 4.15. Found: C, 53.08; H, 3.49; N, 4.12.

REFERENCE EXAMPLE 31

39 g. of α-[(5-Acetylamino-2-methoxycarbonylphenyl)oxy]-γ-butyrolactone was reacted in the same manner as in Reference Example 30, whereby 1.8 g. of 6-acetylamino-4',5'-dihydrospiro[benzo[b]furan-2(3H), 3'(2'H)-furan]-2',3-dione melting at 220°–234° C. and 2.7 g. of 6-diacetylamino-4',5'-dihydrospiro[benzo[b]furan-2(3H),3'(2'H)-furan]-2',3-dione melting at 178° C.

Elemental analysis, for $C_{15}H_{13}O_6N$: Calcd.: C, 59.40; H, 4.32; N, 4.62. Found: C, 59.49; H, 4.21; N, 4.34.

REFERENCE EXAMPLE 32

1.1 g. of α-[(2-Methoxycarbonylphenyl)oxy]-γ-butyrolactone was treated as in Reference Example 17 and the product was recrystallized from ethyl acetate-n-hexane. By the above procedure there was obtained 4',5'-dihydrospiro[benzo[b]furan-2(3H),3'(2'H)-furan]-2',3-dione as colorless needles, m.p. 111°–111.5° C. Yield 330 mg.

REFERENCE EXAMPLE 33

To a solution of 0.408 g. of 4',5'-dihydrospiro[benzo[b]furan-2(3H), 3'(2'H)-furan]-2',3-dione in 3 ml. of concentrated sulfuric acid was added a mixture of 0.35 ml. of nitric acid (d=1.42) and 0.36 ml. of concentrated sulfuric acid, dropwise under ice-cooling, and the mixture was stirred for 2 hours. The reaction mixture was poured into ice-water and the precipitated crystals were collected by filtration, washed with water, dried and recrystallized from ethyl acetate. By the above procedure there was obtained colorless needles of 4',5'-dihydro-5-nitrospiro[benzo[b]furan-2(3H),3'(2'H)-furan]-2',3-dione. m.p. 199°–200° C.

Elemental analysis, for $C_{11}H_7NO_6$: Calcd.: C, 53.02; H, 2.83; N, 5.62. Found: C, 52.89; H, 2.65; N, 5.55.

REFERENCE EXAMPLE 34

A mixture of 4',5'-dihydrospiro[benzo[b]furan-2(3H), 3'(2'H)-furan]-2',3-dione (3 g.) and chlorosulfonic acid was stirred at room temperature and, then, at 40° C. for 1.5 hours. The reaction mixture was poured into ice-water, whereupon white crystals were separated. The crystals were dissolved in tetrahydrofuran, aqueous ammonia (2.2 ml.) was added and the mixture was stirred under ice-cooling for 5 minutes. The powdery precipitates were filtered off, the filtrate was concentrated under reduced pressure and the residue was recrystallized from ethanol-water. By the above procedure there was obtained 5-sulfamoyl-4',5'-dihydrospiro[benzo[b]furan-2(3H),3'(2'H)-furan]-2',3-dione as colorless needles, m.p. 202°–215° C. Yield 2.8 g.

Elemental analysis, for $C_{11}H_9O_6NS$: Calcd.: C, 46.64; H, 3.20; N, 4.95. Found: C, 46.39; H, 3.14; N, 4.87.

EXAMPLE 1

A mixture of 1.75 g. of 4',5'-dihydrospiro[benzo[b]furan-2(3H),3'(2'H)-furan]-2',3-dione, 552 mg. of sodium chloride and 9 ml. of dimethylsulfoxide was stirred in nitrogen gas streams at 155° C. for 2 hours. The reaction mixture was poured into ice-water (ca 150 ml.) and the precipitate was recovered by filtration, washed with water and recrystallized from ethanol-water (3:2). By the above procedure there was obtained 1.21 g. of spiro[benzo[b]furan-2(3H), 1'-cyclopropane]-3-one as colorless needles melting at 89°–90.5° C.

Elemental analysis, for $C_{10}H_8O_2$: Calcd.: C, 74.99; H, 5.03. Found: C, 74.71; H, 4.96.

EXAMPLES 2-15

The following compounds were produced by procedure similar to that described in Example 1.

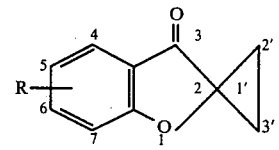

| Ex. No. | Compound R | Melting Point (°C.) | Molecular formula | Elemental Analysis (Upper rank: Calcd.) (Lower rank: Found) | | |
|---|---|---|---|---|---|---|
| | | | | C | H | N |
| 2 | 5-Cl | 120–121 | $C_{10}H_7ClO_2$ | 61.71 | 3.63 | |
| | | | | 61.68 | 3.50 | |
| 3 | 7-$CH_3$ | 126–129 | $C_{11}H_{10}O_2$ | 75.84 | 5.79 | |
| | | | | 75.76 | 5.80 | |
| 4 | 5-Cl, 7-Cl | 116–118 | $C_{10}H_6Cl_2O_2$ | 52.43 | 2.64 | |
| | | | | 52.65 | 2.61 | |
| 5 | 5-$NO_2$ | 107–110 | $C_{10}H_7NO_4$ | 58.54 | 3.44 | 6.83 |
| | | | | 58.85 | 3.50 | 6.68 |
| 6 | 5-$OCH_2Ph$ | 114–116 | $C_{17}H_{14}O_3$ | 76.67 | 5.30 | |
| | | | | 76.53 | 5.18 | |
| 7 | 6-$OCH_3$ | 95–97 | $C_{11}H_{10}O_3$ | 69.46 | 5.30 | |
| | | | | 69.35 | 5.30 | |
| 8 | 5-$OCH_3$ | 86–88 | $C_{11}H_{10}O_3$ | 69.46 | 5.30 | |
| | | | | 69.31 | 5.13 | |
| 9 | 5-$COCH_3$ | 100–103 | $C_{12}H_{10}O_3$ | 71.28 | 4.99 | |
| | | | | 71.07 | 4.82 | |
| 10 | 4-$OCOCH_3$ | 68–71 | $C_{12}H_{10}O_4$ | 66.05 | 4.62 | |
| | | | | 65.89 | 4.52 | |
| 11 | 5-$SO_2NH_2$ | 228–239 (sublimation) | $C_{10}H_9O_4NS$ | 50.20 | 3.79 | 5.86 |
| | | | | 50.19 | 3.71 | 5.79 |
| 12 | 5-$NO_2$, 7-$CH_3$ | 160–162 | $C_{11}H_9O_4N$ | 60.27 | 4.14 | 6.39 |
| | | | | 60.17 | 4.14 | 6.48 |
| 13 | 5-$CH(CH_3)_2$ | b.p.113 (0.4-mmHg) | $C_{13}H_{14}O_2$ | 77.20 | 6.98 | |
| | | | | 77.43 | 7.11 | |
| 14 | 6-NHAc | 171–178 | $C_{12}H_{11}O_3N$ | 66.35 | 5.10 | 6.45 |
| | | | | 66.30 | 5.00 | 6.20 |
| 15 | 5-Cl, 6-NHAc | 185–188 | $C_{12}H_{10}O_3NCl$ | 57.27 | 4.01 | 5.57 |
| | | | | 57.03 | 3.86 | 5.46 |

(Ph represents phenyl and Ac represents acetyl.)

EXAMPLE 16

4',5'-Dihydrospiro[naphtho[2,3-b]furan-2(3H),3'(2'H)furan]-2',3-dione (1.2 g.) was reacted in the same manner as Example 1 and the reaction product was recrystallized from methanol. By the above procedure there was obtained spiro[naphtho[2,3-b]furan-2(3H),1'-cyclopropane]-3-one as colorless needles, m.p. 127°–129° C. Yield 0.75 g.

Elemental analysis, for $C_{14}H_{10}O_2$: Calcd.: C, 79.98; H, 4.79. Found: C, 79.89; H, 4.65.

EXAMPLE 17

5-Hexyl-4',5'-dihydrospiro[benzo[b]furan-2(3H),3'-(2'H)-furan]-2',3-dione was decarboxylated in the same manner as Example 1 to obtain 5-hexylspiro[benzo[b]furan-2(3H),1'-cyclopropane]-3-one as a pale yellowish oil.

IR $_{max}^{film}$ cm$^{-1}$: 1700(CO).

NMR($CDCl_3$)δ: 0.87(3H, t, $CH_3$), 1.36(8H, b, $CH_2$), 1.59(4H, m, cyclopropane), 2.63(2H, t, nuclear $CH_2$), 7.02(1H, d, nuclear H), 7.40(1H, d, nuclear H), 7.48(1H, s, nuclear H).

Elemental analysis, for $C_{16}H_{20}O_2$: Calcd.: C, 78.65; H, 8.25. Found: C, 78.37; H, 8.36.

EXAMPLE 18

In 30 ml. of acetic anhydride was dissolved 0.94 g. of the spiro[benzo[b]furan-2(3H), 1'-cyclopropane]-3-one and, at 60°–70° C., 5.6 g. of copper nitrate was added. The solution was stirred overnight. The reaction mixture was poured into ice-water and extracted with ethyl acetate. The extract was washed with water, dried and distilled to remove the solvent. The residue was fractionated by column chromatography on silica gel into two fractions.

(1) The first fraction was recrystallized from ethyl acetate-n-hexane to yield 5-nitrospiro[benzo[b]furan-2(3H), 1'-cyclopropane]-3-one as colorless prisms melting at 107°–110° C.

Elemental analysis, for $C_{10}H_7NO_4$: Calcd.: C, 58.54; H, 3.44; N, 6.83. Found: C, 58.85; H, 3.50; N, 6.68.

(2) The section fraction was recrystallized from ethyl acetate-hexane to yield 7-nitrospiro[benzo[b]furan-2(3H), 1'-cyclopropane]-3-one as colorless needles melting at 131°–134° C.

Elemental analysis, for $C_{10}H_7NO_4$: Calcd.: C, 58.54; H, 3.44; N, 6.83. Found: C, 58.42; H, 3.37; N, 6.65.

EXAMPLE 19

Spiro[benzo[b]furan-2(3H), 1'-cyclopropane]-3-one (7.0 g.) was added in small portions to fuming nitric acid (70 ml.) previously cooled to −50° C. to −60° C. After stirring for 20 minutes, the reaction mixture was poured into ice-water and the precipitated crystals were collected by filtration, washed with water and recrystallized from ethanol. By the above procedure there was obtained 5-nitrospiro[benzo[b]furan-2(3H),1'-cyclopropane]-3-one as colorless prisms, m.p. 107°–110° C. Yield 7.3 g. This product was in good agreement with the crystals obtained in Example 18.

The mother liquor resulting from the recrystallization was subjected to column chromatography on silicagel for purification, then recrystallized from methanol to afford 5,7-dinitrospiro[benzo[b]furan-2(3H),1'-cyclopropane]-3-one as pale yellow needles melting at 158°–161° C.

Elemental analysis for $C_{10}H_6O_6N_2$: Calcd.: C, 48.01; H, 2.42; N, 11.20. Found: C, 48.03; H, 2.33; N, 11.01.

EXAMPLE 20

5.4 g. of 6-Methoxyspiro[benzo[b]furan-2(3H),1'-cyclopropane]-3-one was dissolved in a mixture of 25 ml. of acetic anhydride and 7 ml. of glacial acetic acid. While keeping the reaction temperature at 10°–15° C., 3 ml. of fuming nitric acid (d=1.52) was added dropwise to the mixture. After stirring for 30 minutes, the reaction mixture was poured into ice-water. The resulting precipitates were collected by filtration, washed with water and recrystallized from ethanol. By the above procedure, there was obtained 6-methoxy-5-nitrospiro[benzo[b]furan-2(3H), 1'-cyclopropane]-3-one as pale yellow prisms melting at 160°–163° C. Yield: 4.5 g.

Elemental analysis, for $C_{11}H_9NO_5$: Calcd.: C, 56.17; H, 3.86; N, 5.96. Found: C, 56.44; H, 3.76; N, 5.80.

EXAMPLE 21

190 mg. of 6-Methoxyspiro[benzo[b]furan-2(3H),1'-cyclopropane]-3-one was added to 2 ml. of fuming nitric acid (d=1.52) at −50° C. while stirring. After 10 minutes, the reaction solution was poured into ice-water, then extracted with ethyl acetate. The extract solution was washed with aqueous solution of sodium bicarbonate, then with saturated saline solution, followed by drying over anhydrous sodium sulfate. Crystals obtained by evaporating the solvent were recrystallized from methanol. By the above procedure, there was obtained 20 mg. of 6-methoxy-5,7-dinitrospiro[benzo[b]furan-2(3H),1'-cyclopropane]-3-one as pale yellow plates melting at 121°–124° C.

Elemental analysis, for $C_{11}H_8O_7N_2$: Calcd.: C, 47.15; H, 2.88; N, 10.00. Found: C, 46.86; H, 2.79; N, 9.83.

EXAMPLE 22

A solution of 5-nitrospiro[benzo[b]furan-2(3H),1'-cyclopropane]-3-one (7.2 g.) in ethanol was stirred in the presence of platinum dioxide and in hydrogen gas streams. After the hydrogen absorption ceased, the catalyst was filtered off and a small amount of HCl-diethyl ether was added to the residue, followed by recrystallization from ethanol. By the above procedure there was obtained 5-aminospiro[benzo[b]furan-2(3H),1'-cyclopropane]-3-one hydrochloride as light-brown needles melting at 139°–142° C.

Elemental analysis, for $C_{10}H_{19}O_2N.HCl$ Calcd.: C, 56.75; H, 4.76; N, 6.62. Found: C, 56.67; H, 4.83; N, 6.67.

EXAMPLE 23

7-Nitrospiro[benzo[b]furan-2(3H),1'-cyclopropane]-3-one as reacted in the same manner as Example 22 and the reaction product was recrystallized from ethanol. By the above procedure there was obtained 7-aminospiro[benzo[b]furan-2(3H),1'-cyclopropane]-3-one as pale brown crystals melting at 135.8° C.

Elemental analysis, for $C_{10}H_{19}O_2N$: Calcd.: C, 68.56; H, 5.18; N, 8.00. Found: C, 68.42; H, 5.11; N, 7.74.

EXAMPLE 24

1.0 g. of 6-Methoxy-5-nitrospiro[benzo[b]furan-2(3H), 1'-cyclopropane]-3-one was reacted in the same manner as Example 22 and the reaction product was recrystallized from ethanol. By the above procedure there was obtained 415 mg. of 5-amino-6-methoxyspiro[benzo[b]furan-2(3H),1'-cyclopropane]-3-one as pale brown prisms melting at 175°–177° C.

Elemental analysis, for $C_{11}H_{11}NO_3$: Calcd.: C, 64.38; H, 5.40; N, 6.83. Found: C, 64.39; H, 5.49; N, 6.71.

EXAMPLE 25

219 mg. of 7-Methyl-5-nitrospiro[benzo[b]-furan-2(3H), 1'-cyclopropane]-3-one was subjected to catalytic reduction as Example 22, and the reaction product was recrystallized from ethanol-water. By the above procedure there was obtained 74 mg. of 5-amino-7-methylspiro[benzo[b]furan-2(3H), 1'-cyclopropane]-3-one as yellow needles melting as 138°–141° C.

Elemental analysis, for $C_{11}H_{11}O_2N$: Calcd.: C, 69.82; H, 5.86; N, 7.40. Found: C, 69.66; H, 5.71; N, 7.43.

EXAMPLE 26

250 mg. of 5,7-Dinitrospiro[benzo[b]furan-2(3H), 1'-cyclopropane]-3-one, 50 mg. of platinum dioxide and 20 ml. of ethanol were stirred in a stream of hydrogen for 1.25 hour under atmospheric pressure. To the reaction mixture was added oxalic acid, and the catalyst was removed by filtration. The filtrate was concentrated under reduced pressure until its volume became above 3 ml. Ether was added to the concentrate, and the resulting powder was collected by filtration. The powder was dissolved in ethanol. To the ethanolic solution was added activated charcoal for decoloration, followed by addition of ether. The precipitating powder was collected by filtration to obtain 5,7-diaminospiro[benzo[b]furan-2(3H),1'-cyclopropane]3-one.½ oxalate.monohydrate as yellowish brown powder.

Elemental analysis, for $C_{10}H_{10}O_2N_2.\frac{1}{2}(COOH)_2.H_2O$: Calcd.: C, 52.17; H, 5.17; N, 11.06. Found: C, 52.12; H, 4.69; N, 10.87.

Use of hydrochloric acid in place of oxalic acid in the above procedure gives 5,7-diaminospiro[benzo[b]furan:2(3H),1'-cyclopropane]-3-one.hydrochloride.-monohydrate melting at a temperature not lower than 300° C.

Elemental analysis, for $C_{10}H_{10}O_2N_2.HCl.H_2O$: Calcd.: C, 49.08; H, 5.35; N, 11.45. Found: C, 48.80; H, 5.13; N, 11.64.

EXAMPLE 27

To a solution of 5-aminospiro[benzo[b]furan-2(3H), 1'-cyclopropane]-3-one (1.35 g.) in pyridine (13.5 ml.) was added carbobenzyloxy chloride (30% toluene solution, 7 g.) under ice-cooling, and the mixture stirred for one hour. The reaction mixture was poured into ice-hydrochloric acid (14 ml.) and extracted with ethyl acetate. The extract was washed with water, dried and concentrated to remove the solvent. The residue was recrystallized from ethanol. By the above procedure there was obtained 5-benzyloxycarbonylaminospiro[benzo[b]furan-2(3H), 1'-cyclopropane]-3-one as pale yellow needles, m.p. 118°-119° C. Yield 1.57 g.

To a solution of this product in acetone (30 ml.) were added potassium hydroxide powder (0.57 g.) and methyl iodide (1 ml.) and the mixture was stirred under ice-cooling for 30 minutes and, then, at room temperature for 4 hours. To this reaction mixture was added dilute hydrochloric acid, followed by extraction with ethyl acetate. The extract was washed with water, dried and distilled under reduced pressure to remove the solvent. The residue was chromatographed on a column of silica gel and the fraction eluted with chloroform was recrystallized from ethanol. By the above procedure there was obtained 5-(N-benzyloxycarbonyl-N-methylamino)spiro[benzo[b]furan-2(3H),1'-cyclopropane]-3-one as colorless needles melting at 79°-81° C. Yield 1.44 g.

This product was dissolved in methanol (129 ml.), and in the presence of 5% palladium-on-carbon, the solution was stirred in hydrogen gas streams for 30 minutes. The catalyst was filtered off, the filtrate was concentrated under reduced pressure and the residue was dissolved in ethanol, followed by addition of HCl-diethyl ether. By the above procedure there was obtained 5-methylaminospiro[benzo[b]furan-2(3H),1'-cyclopropane]-3-one hydrochloride as yellow needles melting at 141°-144° C.

Elemental analysis, for $C_{11}H_{11}O_2N.HCl.\frac{1}{2}H_2O$: Calcd.: C, 56.29; H, 5.58; N, 5.97. Found: C, 56.38; H, 5.15; N, 6.07.

EXAMPLE 28

5-Aminospiro[benzo[b]furan-2(3H),1'-cyclopropane]-3-one (1.75 g.) and 37% formalin (14 ml.) were dissolved in acetonitrile, and under ice-cooling, lithium cyanoborohydride (1.52 g.) was added to the solution portionwise. The mixture was stirred at room temperature for 40 minutes, after which it was neutralized with acetic acid and, then, stirred for 2.5 hours. The solvent was distilled off under reduced pressure, an aqueous solution of sodium hydroxide added to the residue and the mixture extracted with chloroform. The extract was washed with water, dried and concentrated to remove the solvent. The residue was chromatographed on silica gel, elution being carried out with chloroform. To the eluate was added HCl-diethyl ether, followed by recrystallization from ethanol. By the above procedure there was obtained 5-dimethylaminospiro[benzo[b]furan-2(3H), 1'-cyclopropane]-3-one hydrochloride as light-brown needles melting at 136°-140° C. Yield 0.546 g.

NMR($D_2O$) δ: 1.67(2H, m, $CH_2$), 1.93(2H, m, $CH_2$), 3.37(6H, s, $CH_3$), 7.43(1H, d, aromatic ring H), 7.93(2H, m, aromatic ring H).

Elemental analysis, for $C_{12}H_{13}O_2N.HCl$ Calcd.: C, 60.13; H, 5.89; N, 5.85. Found: C, 60.19; H, 5.72; N, 6.00.

EXAMPLE 29

A mixture of 35 g. of 5-nitrospiro[benzo[b]furan-2(3H), 1'-cyclopropane]-3-one, 60 ml. of 37% formalin, 30 ml. of acetic acid, 3 g. of platinum dioxide and 500 ml. of ethanol was subjected to reduction at room temperature under hydrogen pressure of 20 kg/cm². After stopping the hydrogen absorption, the catalyst was removed by filtration, and the filtrate was concentrated under reduced pressure. The concentrate was dissolved in chloroform, washed with 2 N NaOH then with water, followed by drying. Chloroform was removed by evaporation under reduced pressure, and the resulting oily substance was crystallized from ethanol to obtain 26 g. of 5-dimethylaminospiro[benzo[b]furan-2(3H), 1'-cyclopropane]-3-one as yellow cubic crystals melting at 96.5°-97.5° C.

Elemental analysis, for $C_{12}H_{13}O_2N$: Calcd.: C, 70.91; H, 6.45; N, 6.89. Found: C, 71.06; H, 6.39; N, 6.71.

EXAMPLE 30

5-Aminospiro[benzo[b]furan-2(3H),1'-cyclopropane]-3-one (1.75 g.) and acetaldehyde (3 ml.) were dissolved in methanol (105 ml.). The methanolic solution was stirred for 22 hours in hydrogen stream in the presence of platinum dioxide. After removing the catalyst by filtration, the solvent was evaporated off, and the residue was subjected to column-chromatography on silica gel, using carbon tetrachloride - ethyl acetate (10:1) as the eluent. The first fraction was made to hydrochloride with ether saturated with hydrogen chloride, which was recrystallized from ethanol - ether. By the above procedure there was obtained 5-diethylaminospiro[benzo[b]furan-2(3H),1'-cyclopropane]-3-one hydrochloride as pale yellow needles melting at 172°-176° C. Yield 0.86 g.

Elemental analysis, for $C_{14}H_{17}O_2N.HCl$: Calcd.: C, 62.80; H, 6.78; N, 5.23. Found: C, 62.79; H, 6.85; N, 5.10.

The second fraction was made to hydrochloride with ether saturated with hydrogen chloride, which was recrystallized from ethanol-ether to obtain 5-ethylaminospiro[benzo[b]furan-2(3H),1'-cyclopropane]-3-one hydrochloride ¼ hydrate as pale yellow needles melting at 155°-160° C.

Yield 0.129 g.

Elemental analysis, for $C_{12}H_{13}O_2N.HCl.\frac{1}{4}H_2O$: Calcd.: C, 59.02; H, 5.98; N, 5.73. Found: C, 58.94; H, 5.86; N, 5.73.

EXAMPLE 31

A mixture of 5-aminospiro[benzo[b]furan-2(3H),1'-cyclopropane]-3-one(3.0 g.), 1,4-dibromobutane(3.7 g.), sodium hydrogen carbonate (2.89 g.) and N,N-dimethylformamide (150 ml.) was heated under reflux for one hour. The reaction mixture was diluted with water and extracted with ethyl acetate. The extract was washed with water, dried and concentrated to remove the solvent. The residue was chromatographed on silica gel, elution being carried out with chloroform. The first fraction thus obtained was distilled under reduced pressure to recover yellow crystals (1.74 g.). Following addition of HCl-diethyl ether, the product was recrystallized from ethanol. By the above procedure there was obtained yellow needles of 5-(1-pyrrolidinyl)spiro[benzo[b]furan-2(3H),1'-cyclopropane]-3-one hydrochloride. m.p. 136° C.

Elemental analysis for $C_{14}H_{15}O_2N \cdot HCl$ Calcd.: C, 63.27; H, 6.07; N, 5.27. Found: C, 63.26; H, 6.10; N, 5.26.

EXAMPLE 32

A suspension of 5-aminospiro[benzo[b]furan-2(3H),1'-cyclopropane]-3-one (2.62 g.), bis(2-iodoethyl)ether (5.4 g.) and sodium hydrogen carbonate (3.75 g.) in N,N-dimethylformamide (150 ml.) was stirred at 120°–140° C. for 2.5 hours. The reaction solution was poured into water, and extracted with ethyl acetate. The extract was washed with water, dried and removing the solvent by evaporation. The residue was subjected to column-chromatography on silica-gel using chloroform-ethanol (99:1) as the eluent. The eluate was concentrated by evaporation of solvent under reduced pressure to give yellow crystals (1.12 g.), to which was added HCl-ether, then recrystallized from ethanol - ether to obtain 5-morpholinospiro[benzo[b]furan-2(3H),1'-cyclopropane]-3-one hydrochloride as pale brown needles, melting at 128°–131° C.

Yield 0.927 g.

Elemental analysis, for $C_{14}H_{15}O_3N \cdot HCl$: Calcd.: C, 59.68; H, 5.73; N, 4.97. Found: C, 59.59; H, 5.60; N, 4.95.

EXAMPLE 33

5-Aminospiro[benzo[b]furan-2(3H),1'-cyclopropane]-3-one (1.75 g.) was allowed to react with N-benzyl-$\beta,\beta'$-diiododiethylamine (6.8 g.) and sodium hydrogen carbonate (4 g.) in the same manner as in Example 32 to obtain 5-(4-benzyl-1-piperazinyl)spiro[benzo[b]furan-2-(3H),1'-cyclopropane]-3-one as yellow needles melting at 125°–125.5° C.

Yield 0.831 g.

Elemental analysis, for $C_{21}H_{22}O_2N_2$: Calcd.: C, 75.42; H, 6.63; N, 8.38. Found: C, 75.26; H, 6.78; N, 8.41.

EXAMPLE 34

5-Aminospiro[benzo[b]furan-2(3H),1'-cyclopropane]-3-one (1.75 g.) was allowed to react with N-ethyl-$\beta,\beta'$-diiododiethylamine (5.84 g.) and sodium hydrogen carbonate (4 g.) in the same manner as in Example 32 to obtain 5-(4-ethyl-1-piperazinyl)spiro[benzo[b]furan-2(3H),1'-cyclopropane]-3-one oxalate ½ hydrate as yellow needles melting at 175°–179° C.

Elemental analysis, for $C_{16}H_{20}O_2N_2 \cdot C_2H_2O_4 \cdot \frac{1}{2}H_2O$: Calcd.: C, 58.20; H, 6.24; N, 7.54. Found: C, 58.00; H, 6.56; N, 7.24.

EXAMPLE 35

5-Aminospiro[benzo[b]furan-2(3H),1'-cyclopropane]-3-one (0.875 g.) was acetylated with acetic anhydride (7 ml.) and acetic acid (7 ml.) and the acetylation product was recrystallized from ethanol. By the above procedure there was obtained 5-acetylaminospiro[benzo[b]furan-2(3H),1'-cyclopropane]-3-one as yellow prisms melting at 211°–212° C.

Yield 0.426 g.

Elemental analysis, for $C_{12}H_{11}O_3N$: Calcd.: C, 66.35; H, 5.10; N, 6.45. Found: C, 66.37; H, 5.12; N, 6.38.

EXAMPLE 36

To a solution of 5-aminospiro[benzo[b]furan-2(3H),1'-cyclopropane]-3-one (0.519 g.) in pyridine (5 ml.) was added methanesulfonyl chloride (0.28 ml.) under ice-cooling, followed by stirring. The reaction mixture was poured into cooled dilute hydrochloric acid and extracted with ethyl acetate. The extract was washed with water, dried and concentrated to remove the solvent. The residue was recrystallized from ethanol. By the above procedure there was obtained 5-methylsulfonylaminospiro[benzo[b]furan-2(3H),1'-cyclopropane]-3-one as colorless needles melting at 152°–154° C.

Yield 0.38 g.

Elemental analysis, for $C_{11}H_{11}O_4NS$: Calcd.: C, 52.16; H, 4.38; N, 5.53; S, 12.166. Found: C, 52.20; H, 4.37; N, 5.32; S, 12.56.

EXAMPLE 37

A 10% aqueous solution of sodium hydroxide was added to 4-acetoxyspiro[benzo[b]furan-2(3H),1'-cyclopropane]-3-one and the mixture was stirred at room temperature. The reaction mixture was made acidic with hydrochloric acid and extracted with ethyl acetate. The extract was washed with water, dried and distilled to remove the solvent. The residue was recrystallized from petroleum ether. By the above procedure there was obtained 4-hydroxyspiro[benzo[b]furan-2(3H),1'-cyclopropane]-3-one as yellow needles, m.p. 100°–109° C.

Elemental analysis, for $C_{10}H_8O_3$: Calcd.: C, 68.18; H, 4.58. Found: C, 68.38; H, 4.42.

EXAMPLE 38

To a solution of 1.09 g. of 6-acetylaminospiro[benzo[b]furan-2(3H),1'-cyclopropane]-3-one in 50 ml. of methanol was added 0.8 g. of potassium hydroxide, and the mixture was refluxed for 0.5 hour. The solvent was evaporated off under reduced pressure. To the residue was added water, and the precipitating crystals were collected by filtration, washed with water and dried. The crystals were recrystallized from methanol to obtain 6-aminospiro[benzo[b]furan-2(3H),1'-cyclopropane]-3-one as colorless prisms melting at 188°–189° C.

Elemental analysis, for $C_{10}H_9O_2N$: Calcd.: C, 68.56; H, 5.18; N, 8.00. Found: C, 68.34; H, 5.05; N, 7.88.

EXAMPLE 39

6-Acetylamino-5-chlorospiro[benzo[b]furan-2(3H),1'-cyclopropane]-3-one (1.8 g.) was reacted in the same manner as Example 38 and the reaction product was recrystallized from methanol. By the above procedure there was obtained 6-amino-5-chlorospiro[benzo[b]furan-2(3H),1'-cyclopropane]3-one as yellow plates, m.p. 201° C. Yield 1.5 g.

Elemental analysis, for $C_{10}H_8O_2NCl$: Calcd.: C, 57.29; H, 3.85; N, 6.68. Found: C, 57.24; H, 3.74; N, 6.67.

EXAMPLE 40

5-Benzyloxyspiro[benzo[b]furan-2(3H),1'-cyclopropane]-3-one (3.3 g.) was debenzylated by catalytic reduction in methanol. By this procedure there was obtained 5-hydroxyspiro[benzo[b]furan-2(3H),1'-cyclopropane]-3-one as pale yellow needles, m.p. 180°-185° C. Yield 1.8 g.

Elemental analysis, for $C_{10}H_8O_3$: Calcd.: C, 68.18; H, 4.58. Found: C, 68.12; H, 4.44.

EXAMPLE 41

A mixture of 4-hydroxyspiro[benzo[b]furan-2(3H),1'-cyclopropane]-3-one, (0.176 g.) potassium carbonate (0.276 g.), β-diethylaminoethyl chloride (0.215 g.) and N,N-dimethylformamide (5 ml.) was stirred at room temperature for 3 hours. The reaction mixture was diluted with water and extracted with ethyl acetate. The extract was washed with water, dried and distilled to remove the solvent. The residue was purified by column chromatography on silica gel, using chloroform as the eluent. The product was treated with HCl-saturated diethyl ether and the resultant hydrochloride was recrystallized from ethanol-diethyl ether. By the above procedure there was obtained 4-(2-diethylaminoethyloxy)spiro[benzo[b]furan-2(3H),1'-cyclopropane]-3-one hydrochloride as colorless needles, m.p. 160°-168° C. Yield 0.221 g.

Elemental analysis, for $C_{16}H_{21}O_3N \cdot HCl$: Calcd.: C, 61.63; H, 7.11; N, 4.49. Found: C, 61.38; H, 7.23; N, 4.38.

EXAMPLE 42

5-Hydroxyspiro[benzo[b]furan-2(3H),1'-cyclopropane]-3-one (1.06 g.) was reacted in the same manner as Example 41 to obtain 5-(2-diethylaminoethyloxy)spiro[benzo[b]furan-2(3H),1'-cyclopropane]-3-one as colorless oil. Nuclear magnetic resonance spectrum (δ, in deuteriochloroform): 1.07(6H, t, $CH_3$), 1.63(4H, m, 2',3'-$CH_2$), 2.64(4H, q, $NCH_2CH_3$), 2.88(2H, t, $NCH_2CH_2O$), 4.04(2H, t, $CH_2O$), 6.95-7.40(3H, m, aromatic ring H).

EXAMPLE 43

5-Aminospiro[benzo[b]furan-2(3H),1'-cyclopropane]-3-one (0.747 g.) and calcium carbonate (0.47 g.) were suspended in a mixture of carbon tetrachloride (20 ml.) and methylene chloride (5 ml.). The suspension was cooled to −17° C., then bromine (0.22 ml.) was added thereto dropwise, followed by stirring for 45 minutes. The reaction mixture was poured into ice-water, then extracted with ethyl acetate. The extract was washed with water and dried. The solvent was evaporated off, and the residue was recrystallized from ethanol-water. By the above procedure there was obtained 5-amino-4-bromospiro[benzo[b]furan-2(3H),1'-cyclopropane]-3-one as yellow needles melting at 167°-170° C. Yield 0.6 g.

Elemental analysis, for $C_{10}H_8O_2NBr$: Calcd.: C, 47.27; H, 3.19; N, 5.51. Found: C, 47.58; H, 3.12; N, 5.64.

EXAMPLE 44

A suspension of 5-dimethylaminospiro[benzo[b]furan-2(3H),1'-cyclopropane]-3-one (0.455 g.) and calcium carbonate (0.246 g.) in carbon tetrachloride (10 ml.) was reacted in the same manner as Example 43 to obtain 4-bromo-5-dimethylaminospiro[benzo[b]furan-2(3H),1'-cyclopropane]-3-one as brown needles melting at 79°-81° C. Yield 0.213 g.

Elemental analysis, for $C_{12}H_{12}O_2NBr$: Calcd.: C, 51.08; H, 4.29; N, 4.97. Found: C, 50.87; H, 4.13; N, 5.03.

EXAMPLE 45

A solution of 5-aminospiro[benzo[b]furan-2(3H),1'-cyclopropane]-3-one (0.181 g.) and pyridine (0.083 mg.) in tetrahydrofuran (5 ml.) was cooled to −17° C. To the solution was added dropwise iodobenzenedichloride (0.282 g.), which had been prepared by conventional method, dissolved in tetrahydrofuran (1.5 ml.) over 50 minutes, followed by stirring for 1 hour. The reaction mixture was poured into ice-water and extracted with ethyl acetate. The extract was washed with water, dried and the solvent was evaporated off. The residue was subjected to column-chromatography, using chloroform as the eluent. The first fraction was concentrated under reduced pressure to remove the solvent. By the above procedure, there was obtained 5-amino-4-chlorospiro[benzo[b]furan-2(3H),1'-cyclopropane]-3-one as yellow crystals. Yield 0.038 g.

Mass spectrum: $C_{12}H_{12}O_2NCl$, molecular ion peak (209).

REFERENCE EXAMPLES 35-38

The following compounds were produced by procedure similar to that described in Reference Example 5.

| Reference Example | Compound R | m.p. (°C.) | Molecular formula | Elemental analysis Upper rank: Calcd. Lower rank: Found | |
|---|---|---|---|---|---|
| | | | | C | H |
| 35 | 5-Ph | 112-114 | $C_{18}H_{16}O_5$ | 69.22 | 5.16 |
| | | | | 69.41 | 5.07 |
| 36 | 5-COPh | 98-102 | $C_{19}H_{16}O_6$ | 67.05 | 4.75 |
| | | | | 67.32 | 4.77 |
| 37 | 5-$COC_2H_5$ | 109-111 | $C_{15}H_{16}O_6$ | 61.64 | 5.52 |
| | | | | 61.63 | 5.56 |
| 38 | 5-$SCH_3$ | 60-63 | $C_{13}H_{14}O_5S$ | 55.30 | 5.00 |
| | | | | 55.09 | 4.93 |

(Ph represents phenyl)

REFERENCE EXAMPLE 39

α-[(2-Methoxycarbonyl-4-methylthiophenyl)oxy]-γ-butyrolactone (1.128 g.) was dissolved in dichloromethane (24 ml.) and to the solution m-chloro-perbenzoic acid (1.72 g.) was added in small portions. After stirring for one hour, the mixture was extracted with chloroform. The extract was washed with aqueous solution of sodium hydrogen carbonate, aqueous solution of sodium hydrosulfite and water in the order mentioned, and dried. The solvent was evaporated off under reduced pressure and the residue was recrystallized from ethyl acetate-hexane to give α-[(2-methoxycarbonyl-4-methylsulfonylphenyl)oxy]-γ-butyrolactone (1.089 g.) as colorless needles melting at 102°-105° C.

Elemental analysis, for $C_{13}H_{14}O_7S$: Calcd.: C, 49.68; H, 4.49. Found: C, 49.67; H, 4.42.

REFERENCE EXAMPLES 40-44

The following compounds were obtained by procedure similar to that of Reference Example 17.

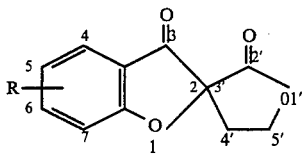

| Reference Example | Compound R | m.p. (°C.) | Molecular formula | Elemental analysis Upper rank: Calcd. Lower rank: Found | |
|---|---|---|---|---|---|
| | | | | C | H |
| 40 | 5-Ph | 193–195 | $C_{17}H_{12}O_4$ | 72.82 | 4.32 4.19 |
| 41 | 5-COPh | 197–200 | $C_{18}H_{12}O_5$ | 70.13 69.95 | 3.92 3.78 |
| 42 | 5-COC$_2$H$_5$ | 163–165 | $C_{14}H_{12}O_5$ | 64.61 64.70 | 4.65 4.57 |
| 43 | 5-SCH$_3$ | 100–102 | $C_{12}H_{10}O_4S$ | 57.59 57.82 | 4.03 3.90 |
| 44 | 5-SO$_2$CH$_3$ | 220–226 | $C_{12}H_{10}O_6S$ | 51.06 50.97 | 3.57 3.52 |

(Ph represents phenyl)

EXAMPLE 46

5-Aminospiro[benzo[b]furan-2(3H),1′-cyclopropane]-3-one (2 g.) was allowed to react with acetone (5 ml.) in the same manner as Example 28, and the product was recrystallized from ethyl ether-hexane to give 5-isopropylamino[benzo[b]furan-2(3H),1′-cyclopropane]-3-one (1.3 g.) as yellow prisms melting at 69°–71° C.

Elemental analysis, for $C_{13}H_{15}O_2N$: Calcd.: C, 71.86; H, 6.96; N, 6.45. Found: C, 71.94; H, 7.03; N, 6.51.

EXAMPLE 47

A mixture of 7-nitrospiro[benzo[b]furan-2(3H),1′-cyclopropane]-3-one (10 g.), formalin (37% formaldehyde, 10 ml.), trimethylamine hydrochloride (2 g.) and Raney nickel (10 g.) in ethanol (500 ml.) was subjected to reduction at 49°–56° C. for 3 hours under hydrogen pressure of 50 kg/cm². After removing the catalyst by filtration, and the filtrate was concentrated under reduced pressure. The concentrate was dissolved in dichloromethane and the solution was washed with 5% aqueous solution of sodium hydrogen carbonate then with water, followed by drying. The solvent was evaporated off and the residue was subjected to column-chromatography on silica-gel. The first fraction eluted with hexane-ethyl acetate (9:1) was recrystallized from ethanol to give 7-dimethylaminospiro[benzo[b]furan-2(3H),1′-cyclopropane]-3-one (5.87 g.) as yellow needles melting at 68.3° C.

Elemental analysis, for $C_{12}H_{13}O_2N$: Calcd.: C, 70.92; H, 6.45; N, 6.89. Found: C, 70.89; H, 6.41; N, 6.71.

The second fraction was recrystallized from ethanol to give 7-methylaminospiro[benzo[b]furan-2(3H),1′-cyclopropane]-3-one (2.08 g.) as yellow needles melting at 98.2° C.

Elemental analysis, for $C_{11}H_{11}O_2N$: Calcd.: C, 69.83; H, 5.86; N, 7.40. Found: C, 70.10; H, 5.86; N, 7.36.

EXAMPLE 48

7-Aminospiro[benzo[b]furan-2(3H),1′-cyclopropane]-3-one (3.5 g) and 1,4-dibromobutane (4.3 g.) were reacted in the same manner as Example 31, and the product was recrystallized from ethanol to give 7-(1-pyrrolidinyl)spiro[benzo[b]furan-2(3H),1′-cyclopropane]-3-one (0.87 g.) as yellow needles melting at 101.5° C.

Elemental analysis, for $C_{14}H_{15}O_2N$: Calcd.: C, 73.34; H, 6.59; N, 6.11. Found: C, 73.10; H, 6.52; N, 6.02.

EXAMPLE 49

A mixture of 7-aminospiro[benzo[b]furan-2(3H),1′-cyclopropane]-3-one (1.75 g.) and ethylbromide (5.45 g.) and sodium hydrogen carbonate (1.68 g.) in N,N-dimethylformamide (50 ml.) was heated at 100° C. for 4 hours. The reaction mixture was diluted with water and extracted with ethyl acetate. The extract was washed with water and dried, then the solvent was evaporated off. The residue was subjected to column-chromatography on silica-gel. The first fraction eluted with hexane-ethyl acetate (97:3) was recrystallized from ethanol to give 7-diethylaminospiro[benzo[b]furan-2(3H),1′-cyclopropane]-3-one (0.801 g.) as yellow needles melting at 39.3° C.

Elemental analysis, for $C_{14}H_{17}O_2N$: Calcd.: C, 72.70; H, 7.41; N, 6.06. Found: C, 72.83; H, 7.42; N, 6.11.

The second fraction eluted with hexane-ethyl acetate (95:5) was recrystallized from ethanol to give 7-ethylaminospiro[benzo[b]furan-2(3H),1′-cyclopropane]-3-one (0.204 g.) as pale yellow needles melting at 80.6° C.

Elemental analysis, for $C_{12}H_{13}O_2N$: Calcd.: C, 70.92; H, 6.45; N, 6.89. Found: C, 70.71; H, 6.49; N, 6.81.

EXAMPLE 50

5-Aminospiro[benzo[b]furan-2(3H),1′-cyclopropane]-3-one (10 g.), ethylene oxide (5 g.) and methanol (150 ml.) were allowed to react in a sealed tube at 70° C. for 16 hours, and after cooling the solvent was evaporated off under reduced pressure. The residue was recrystallized from ethyl acetate-hexane to give 5-bis(β-hydroxyethyl)aminospiro[benzo[b]furan-2(3H),1′-cyclopropane]-3-one (12.9 g.) as yellow needles melting at 96°–97° C.

Elemental analysis, for $C_{14}H_{17}O_4N$: Calcd.: C, 63.86; H, 6.51; N, 5.32. Found: C, 63.75; H, 6.54; N, 5.23.

The crystals obtained from mother liquor of the above recrystallization was subjected to column-chromatography on silica-gel, and the fraction eluted with 2% ethanol-methylene chloride was recrystallized from ethyl acetate-hexane to give 5-(β-hydroxyethyl)aminospiro[benzo[b]furan-2(3H),1′-cyclopropane]-3-one (1.6 g.) as yellow needles melting at 74°–75° C.

Elemental analysis, for $C_{12}H_{13}O_3N$: Calcd.: C, 65.74; H, 5.98; N, 6.39. Found: C, 65.71; H, 6.02; N, 6.23.

EXAMPLE 51

7-Aminospiro[benzo[b]furan-2(3H),1′-cyclopropane]-3-one (350 mg.) was reacted in the same manner as Example 50, and the product was subjected to column-chromatography on silica-gel. The first fraction eluted with chloroform was recrystallized from ethyl acetate-hexane to give 7-(β-hydroxyethyl)aminospiro[benzo[b]furan-2(3H),1′-cyclopropane]-3-one as yellow needles melting at 74°–77° C.

Elemental analysis, for $C_{12}H_{13}O_3N$: Calcd.: C, 65.74; H, 5.98; N, 6.39. Found: C, 65.96; H, 5.98; N, 6.19.

The second fraction eluted with 2% ethanol-chloroform was recrystallized from ethyl acetate-hexane to give 7-bis(β-hydroxyethyl)aminospiro[benzo[b]furan-2(3H),1′-cyclopropane]-3-one as yellow needles melting at 74°–76° C.

Elemental analysis, for $C_{14}H_{17}O_4N$: Calcd.: C, 63.86; H, 6.51; N, 5.32. Found: C, 63.67; H, 6.51; N, 5.35.

EXAMPLE 52

To a solution of 5-aminospiro[benzo[b]furan-2(3H),1'-cyclopropane]-3-one (1.75 g.) in methanol (10 ml.) and acetic acid (5 ml.) was added dropwise 2 ml. of aqueous solution of sodium cyanate (130 mg.), and the mixture was stirred for 2 hours at room temperature. To the reaction mixture was added ice-water, and the precipitated crystals were collected by filtration and recrystallized from ethanol to give colorless needles of 5-ureidospiro[benzo[b]furan-2(3H),1'-cyclopropane]-3-one (0.74 g.).

M.p. 250°–252° C.

Elemental analysis, for $C_{11}H_{10}O_3N_2$: Calcd.: C, 60.54; H, 4.62; N, 12.84. Found: C, 60.42; H, 4.42; N, 12.94.

EXAMPLE 53

5-Aminospiro[benzo[b]furan-2(3H),1'-cyclopropane]-3-one (1.75 g.) and methyl isocyanate (1 ml.) were stirred in tetrahydrofuran for 2 hours at room temperature. The solvent was evaporated off under reduced pressure, and the residue was recrystallized from ethanol to give yellow prisms of 5-methylureidospiro[benzo[b]furan-2(3H),1'-cyclopropane]-3-one (1.06 g.).

M.p. 196°–204° C.

Elemental analysis, for $C_{12}H_{12}O_3N$: Calcd.: C, 62.06; H, 5.21; N, 12.06. Found: C, 61.87; H, 5.11; N, 11.67.

EXAMPLE 54

5-Aminospiro[benzo[b]furan-2(3H),1'-cyclopropane]-3-one (1.75 g.) and methyl isothiocyanate (1.1 g.) were stirred in acetonitrile (60 ml.) at room temperature for 15 hours, and then the mixture was refluxed under heating for 3 hours. The solvent was evaporated off under reduced pressure, and the residue was recrystallized from methanol to give yellow prisms of 5-methylthioureidospiro[benzo[b]furan-2(3H),1'-cyclopropane]-3-one (1.62 g.). m.p. 191°–194° C.

Elemental analysis, for $C_{12}H_{12}O_2N_2S$: Calcd.: C 58.04; H, 4.87; N, 11.28. Found: C, 58.07; H, 4.87; N, 11.00.

EXAMPLE 55

5-Aminospiro[benzo[b]furan-2(3H),1'-cyclopropane]-3-one (1.75 g.) was dissolved in conc. HCl (2.5 ml.) and ice-water (20 ml.), and to the solution was added dropwise 2 ml of aqueous solution of sodium nitrite (0.7 g.) under ice-cooling. After stirring for one hour and adding toluene (5 ml.), the solution was neutralized with sodium hydrogen carbonate at −20° C. To 18 ml of another aqueous solution of cuprous cyanide prepared from cuprous chloride (2.4 g.) and potassium cyanide (4.4 g.) was added ethyl acetate (20 ml.), and, to the mixture was added, under ice-cooling and stirring, the above neutralized solution of diazonium salt. The mixture was stirred for half an hour at room temperature and further stirred for half an hour at 70° C. The insolubles were removed by filtration, and the filtrate was extracted with ethyl acetate. The extract was washed with aqueous solution of sodium carbonate, diluted hydrochloric acid and water in the order mentioned, and dried. The solvent was evaporated off under reduced pressure, and the obtained residue was recrystallized from methanol to give colorless needles of 5-cyanospiro[benzo[b]furan-2(3H),1'-cyclopropane]-3-one (1.4 g.) m.p. 148°–149° C.

Elemental analysis, for $C_{11}H_7O_2N$: Calcd.: C, 71.35; H, 3.81; N, 7.56. Found: C, 71.13; H, 3.70; N, 7.39.

EXAMPLE 56

5-Acetylspiro[benzo[b]furan-2(3H),1'-cyclopropane]-3-one (13.5 g.) was added to 300 ml. of aqueous solution of sodium hypochlorite. To the mixture was further added a small amount of surface active agent (polyoxyethylene octyl phenyl ether), and the mixture was stirred at 60° C. for 3 hours. After cooling, the reaction mixture was diluted with water, and to the mixture was added 40% aqueous solution of sodium hydrogen sulfite. The reaction mixture was made acidic with hydrochloric acid, and resulting crystals were collected by filtration. After washing with water and drying, the crystals were recrystallized from ethanol to give colorless needles of 5-carboxyspiro[benzo[b]furan-2(3H),1'-cyclopropane]-3-one (12.68 g.). m.p. 215°–228° C.

Elemental analysis, for $C_{11}H_8O_4$: Calcd.: C, 64.70; H, 3.95. Found: C, 64.75; H, 3.84.

EXAMPLE 57

5-Carboxyspiro[benzo[b]furan-2(3H),1'-cyclopropane]-3-one (2 g.) and sodium hydrogen carbonate (1.25 g.) were suspended in acetone (50 ml.) and N,N-dimethylformamide (5 ml.) and, under stirring, dimethyl sulfate (2 ml.) was added dropwise to the mixture. The reaction mixture was refluxed under heating for 24 hours, and, after cooling, the solvent was evaporated off under reduced pressure. The residue was diluted with water and the solution was extracted with ethyl acetate. The extract was washed with aqueous solution of sodium hydrogen carbonate and dried. After removing the solvent by evaporation under reduced pressure, the residue was recrystallized from methanol to give colorless needles of 5-methoxycarbonylspiro[benzo[b]furan-2(3H),1'-cyclopropane]-3-one (1.25 g.).

M.p. 89°–91° C.

Elemental analysis, for $C_{12}H_{10}O_4$: Calcd.: C, 66.05; H, 4.62. Found: C, 66.19; H, 4.62.

EXAMPLE 58

To a solution of 5-carboxyspiro[benzo[b]furan-2(3H),1'-cyclopropane]-3-one (1.02 g.) in 30 ml. of tetrahydrofuran was added triethylamine (0.5 g.) and, under stirring at −18° C., isobutyl chlorocarbonate (0.75 g.) was added dropwise to the solution. After stirring for 30 minutes, 2-(diethylamino)ethylamine (0.58 g.) was added and the mixture was stirred at room temperature for 3 hours. The solvent was evaporated off under reduced pressure, and the residue was dissolved in ethanol. To the solution was added oxalic acid to form oxalate and, after cooling, the resulting crystals were collected by filtration to give colorless needles of 5-(2-diethylaminoethyl)carbamoylspiro[benzo[b]furan-2(3H),1'-cyclopropane]-3-one oxalate (1.08 g.).

M.p. 174°–179° C.

Elemental analysis, for $C_{17}H_{22}O_3N_2 \cdot C_2H_2O_4$: Calcd.: C, 58.15; H, 6.17; N, 7.14. Found: C, 57.92; H, 6.27; N, 7.15.

EXAMPLE 59

5-Carboxyspiro[benzo[b]furan-2(3H), 1'-cyclopropane]-3-one (2.04 g.), triethylamine (1.4 ml.), isobutyl chlorocarbonate (1.5 g.) and N-ethyl-2-aminomethylpyrrolidine (1.4 g.) were allowed to react in the same manner as Example 58. The product was converted to oxalate by a known procedure and recrystallization from ethanol gave colorless prisms of 5-(1-ethyl-2-pyrrolidinyl)methylcarbamoylspiro[benzo[b]furan-2(3H), 1'-cyclopropane]-3-one (1.567 g.).

M.p. 161°–166° C.

Elemental analysis, for $C_{18}H_{22}O_3N_2 \cdot C_2H_2O_4$: Calcd.: C, 59.40; H, 5.98; N, 6.93. Found: C, 59.13; H, 6.02; N, 6.75.

EXAMPLES 60–64

The following compounds were obtained by procedure similar to that of Example 1.

[Structure diagram: spiro[benzo[b]furan-2(3H),1'-cyclopropane]-3-one with R substituent at position 5, positions labeled 4,5,6,7 on benzene ring, 2,3 on furanone, 1',2',3' on cyclopropane, O at position 1, =O at position 3]

| Reference Example | Compound R | m.p. (°C.) | Molecular formula | Elemental analysis Upper rank: Calcd. Lower rank: Found | |
|---|---|---|---|---|---|
| | | | | C | H |
| 60 | 5-Ph | 116–121 | $C_{16}H_{12}O_2$ | 81.34 | 5.12 |
| | | | | 81.65 | 5.00 |
| 61 | 5-COPh | 89–91 | $C_{17}H_{12}O_3$ | 77.26 | 4.58 |
| | | | | 77.30 | 4.33 |
| 62 | 5-COC$_2$H$_5$ | 75–77 | $C_{13}H_{12}O_3$ | 72.21 | 5.59 |
| | | | | 72.16 | 5.52 |
| 63 | 5-SCH$_3$ | 64–66 | $C_{11}H_{10}O_2S$ | 64.06 | 4.89 |
| | | | | 63.79 | 4.76 |
| 64 | 5-SO$_2$CH$_3$ | 157–159 | $C_{11}H_{10}O_4S$ | 55.45 | 4.23 |
| | | | | 55.37 | 4.16 |

(Ph represents phenyl)

EXAMPLE 65

To a solution of 5-methylthiospiro[benzo[b]furan-2(3H), 1'-cyclopropane]-3-one (103.1 mg.) in dichloromethane (2.1 ml.) was added in small portions of m-chloroperbenzoic acid (215.7 mg.) under stirring. After stirring for one hour, the reaction mixture was diluted with water and extracted with chloroform. The extract was washed with aqueous solution of sodium hydrogen carbonate, aqueous solution of sodium hydrosulfite and water in that order, and after drying the solvent was removed by evaporation under reduced pressure. The residue was recrystallized from ethanol-water to give colorless needles of 5-methylsulfonylspiro[benzo[b]furan-2(3H), 1'-cyclopropane]-3-one (85 mg.). This product was identical with the compound of Example 64 in melting point and spectral data.

EXAMPLE 66

5-Methylthiospiro[benzo[b]furan-2(3H), 1'-cyclopropane]-3-one (600 mg.) and m-chloroperbenzoic acid (627 mg.) were allowed to react in the same manner as Example 65. The product was recrystallized from ethyl acetate-hexane to give colorless prisms of 5-methylsulfinylspiro[benzo[b]furan-2(3H), 1'-cyclopropane]-3-one (493 mg.). m.p. 87°–90° C.

Elemental analysis, for $C_{11}H_{10}O_3S$: Calcd.: C, 59.44; H, 4.54. Found: C, 59.31; H, 4.57.

EXAMPLE 67

A solution of 5-cyanospiro[benzo[b]furan-2(3H), 1'-cyclopropane]-3-one (0.2 g.) in 10 ml. of ethanol and 10 ml of 2 N aqueous solution of sodium hydroxide was subjected to catalitic reduction in the presence of Raney-nickel under hydrogen streams and at an ordinary temperature and pressure. After finishing the absorption of hydrogen, the catalyst was removed by filtration, and the filtrate was diluted with water and extracted with chloroform. The extract was washed with water and, after drying, the solvent was removed by evaporation under reduced pressure. The residue was dissolved in methanol and to the solution was added oxalic acid to form oxalate. Recrystallization from methanol-ethyl acetate gave pale brown needles of 5-aminomethylspiro[benzo[b]furan-2(3H), 1'-cyclopropane]-3-one oxalate.

M.p. 192°–195° C.

Elemental analysis, for $C_{11}H_{11}O_2N \cdot C_2H_2O_4$: Calcd.: C, 55.91; H, 4.69; N, 5.02. Found: C, 55.74; H, 4.60; N, 4.93.

EXAMPLE 68

To a solution of 5-cyanospiro[benzo[b]furan-2(3H), 1'-cyclopropane]-3-one (185 mg.) in ethanol (10 ml.) were added dropwise 5.5 ml. of 7% aqueous solution of hydrogen peroxide and 3.7 ml. of ethanol, then, to the mixture, was added 2 N aqueous solution of sodium hydroxide to adjust pH 10 and the solution was stirred at 60° C. for 2 hours. After cooling, the reaction mixture was neutralized with diluted hydrochloric acid and diluted with ice-water. The precipitating crystals were collected by filtration, washed with water and recrystallized from ethanol to give colorless needles of 5-carbamoylspiro[benzo[b]furan-2(3H), 1'-cyclopropane]-3-one (106 mg.). m.p. 243°–244° C.

Elemental analysis, for $C_{11}H_9O_3N$: Calcd.: C, 65.02; H, 4.46; N, 6.89. Found: C, 65.19; H, 4.39; N, 6.78.

Examples of preparations ready for administration

When use of the compound of this invention is intended as an antiulcer agent, types of the preparation can be exemplified as follows.

| 1. Tablet | |
|---|---|
| (1) 5-Acetylspiro[benzo[b]furan-2(3H), 1'-cyclopropane]-3-one | 50 g. |
| (2) Lactose | 50 g. |
| (3) Corn-starch | 29 g. |
| (4) Magnesium stearate | 1 g. |
| 1000 tablets | 130 g. |

(1), (2) and 17 g. of corn-starch were granulated together with paste prepared from 7 g. of corn-starch. To this granule were added 5 g. of corn-starch and (4), and the mixture was compressed by a tabletting machine to prepare 1000 tablets of 7 mm. diameter, each containing 50 mg. of (1).

| 2. Capsule | |
|---|---|
| (1) 5-Dimethylaminospiro[benzo[b]furan-2(3H), 1'-cyclopropane]-3-one | 50 g. |
| (2) Lactose | 100 g. |
| (3) Cellulose fine powder | 45 g. |
| (4) Magnesium stearate | 5 g. |
| 1000 capsules | 200 g. |

All the materials were mixed and filled into 1000 capsules (gelatin capsule No. 3 defined in Japanese Pharmacopoeia 8th edition) to prepare capsules each containing 50 mg. of (1).

What we claim is:

1. A compound of the formula

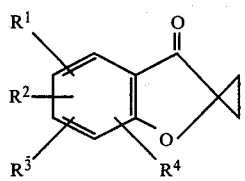

wherein
each of $R^1$, $R^2$, $R^3$ and $R^4$ is independently hydrogen, $C_{1-6}$ alkyl, nitro, halogen, hydroxyl, $C_{1-6}$ alkoxy, mono- or di-$C_{1-4}$ alkylamino-$C_{1-6}$ alkoxy, phenyl-$C_{1-4}$ alkyloxy, $C_{2-6}$ alkanoyloxy, benzoyloxy, $C_{2-6}$ alkanoyl, benzoyl, sulfamoyl, carboxyl, $C_{2-6}$ alkoxycarbonyl, carbamoyl, $C_{1-4}$ alkylcarbamoyl, di-$C_{1-4}$ alkylamino-$C_{1-4}$ alkylcarbamoyl, N-$C_{1-4}$ alkylpyrrolidinyl-$C_{1-4}$ alkylcarbamoyl, ureido, $C_{1-4}$ alkylureido, thioureido, $C_{1-4}$ alkylthioureido, $C_{1-4}$ alkylthio, $C_{1-4}$ alkylsulfinyl, $C_{1-4}$ alkylsulfonyl, aminomethyl, mono- or di-$C_{1-4}$ alkylaminomethyl, cyano, phenyl, amino, mono- or bis-($\beta$-hydroxyethyl)amino, $C_{1-4}$ alkylamino, di-$C_{1-4}$ alkylamino, $C_{2-4}$ alkanoylamino, $C_{1-4}$ alkanesulfonylamino, 1-pyrrolidinyl, piperidino, a 1-piperazinyl group, or morpholino, said 1-piperazinyl group being unsubstituted or substituted at the nitrogen atom of its 4-position by $C_{1-4}$ alkyl, phenyl-$C_{1-4}$ alkyl or $C_{2-4}$ alkanoyl, or
two of $R^1$, $R^2$, $R^3$ and $R^4$ together form —CH=CH—CH=CH— at adjacent carbon atoms of the benzene ring.

2. A compound of the formula

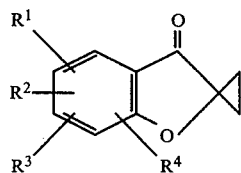

wherein
each of $R^1$, $R^2$, $R^3$ and $R^4$ is independently hydrogen, $C_{1-6}$ alkyl, nitro, halogen, hydroxyl, $C_{1-6}$ alkoxy, mono- or di-$C_{1-4}$ alkylamino-$C_{1-6}$ alkoxy, phenyl-$C_{1-4}$ alkyloxy, $C_{2-6}$ alkanoyloxy, benzoyloxy, $C_{2-6}$ alkanoyl, benzoyl, sulfamoyl, amino, $C_{1-4}$ alkylamino, di-$C_{1-4}$ alkylamino, $C_{2-4}$ alkanoylamino, $C_{1-4}$ alkanesulfonylamino, 1-pyrrolidinyl, piperidino, a 1-piperazinyl group, or morpholino, said 1-piperazinyl group being unsubstituted or substituted at the nitrogen atom of its 4-position by $C_{1-4}$ alkyl, phenyl-$C_{1-4}$ alkyl or $C_{2-4}$ alkanoyl, or
two of $R^1$, $R^2$, $R^3$ and $R^4$ together form —CH=CH—CH=CH— at adjacent carbon atoms of the benzene ring.

3. A compound according to claim 2, wherein $R^1$ is di-$C_{1-4}$ alkylamino and $R^2$, $R^3$ and $R^4$ are hydrogen.

4. A compound according to claim 2, wherein $R^1$ is $C_{2-6}$ alkanoyl and $R^2$, $R^3$ and $R^4$ are hydrogen.

5. The compound according to claim 2, which is spiro[benzo[b]furan-2-(3H),1'-cyclopropane]-3-one.

6. The compound according to claim 2, which is spiro[naphtho[2,3-b]furan-2(3H),1'-cyclopropane]-3-one.

7. The compound according to claim 2, which is 5-nitrospiro[benzo[b]furan-2-(3H),1'-cyclopropane]-3-one.

8. The compound according to claim 2, which is 5-aminospiro[benzo[b]furan-2(3H),1'-cyclopropane]-3-one.

9. The compound according to claim 2, which is 5-methylaminospiro[benzo[b]furan-2(3H),1'-cyclopropane]-3-one.

10. A compound of the formula

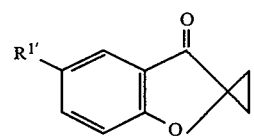

wherein $R^{1'}$ is di-$C_{1-4}$ alkylamino, or
a pharmaceutically acceptable salt thereof.

11. The compound according to claim 10, which is 5-dimethylaminospiro[benzo[b]furan-2(3H),1'-cyclopropane]-3-one.

12. The compound according to claim 10, which is 5-diethylaminospiro[benzo[b]furan-2(3H),1'-cyclopropane]-3-one.

13. A compound of the formula

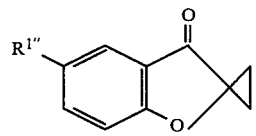

wherein $R^{1''}$ is $C_{2-6}$ alkanoyl.

14. The compound according to claim 13, which is 5-acetylspiro[benzo[b]furan-2(3H),1'-cyclopropane]-3-one.

15. A pharmaceutical composition for managing peptic ulcer which comprises, as an active ingredient, an effective amount of a compound of the formula

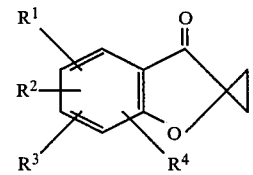

wherein
each of $R^1$, $R^2$, $R^3$ and $R^4$ is independently hydrogen, $C_{1-6}$ alkyl, nitro, halogen, hydroxyl, $C_{1-6}$ alkoxy, mono- or di-$C_{1-4}$ alkylamino-$C_{1-6}$ alkoxy, phenyl-$C_{1-4}$ alkyloxy, $C_{2-6}$ alkanoyloxy, benzoyloxy, $C_{2-6}$ alkanoyl, benzoyl, sulfamoyl, carboxyl, $C_{2-6}$ alkoxycarbonyl, carbamoyl, $C_{1-4}$ alkylcarbamoyl, di-$C_{1-4}$ alkylamino-$C_{1-4}$ alkylcarbamoyl, N-$C_{1-4}$ alkylpyrrolidinyl-$C_{1-4}$ alkylcarbamoyl, ureido, $C_{1-4}$ alkylureido, thioureido, $C_{1-4}$ alkylthioureido, $C_{1-4}$ alkylthio, $C_{1-4}$ alkylsulfinyl, $C_{1-4}$ alkylsulfonyl, aminomethyl, mono- or di-$C_{1-4}$ alkylaminomethyl, cyano, phenyl, amino, mono- or bis-($\beta$-hydroxyethyl)amino, $C_{1-4}$ alkylamino, di-$C_{1-4}$ alkylamino, $C_{2-4}$ alkanoylamino, $C_{1-4}$ alkanesulfonylamino, 1- pyrrolidinyl, piperidino, a 1-piperazinyl group, or morpholino, said 1-piperazinyl group being unsubstituted or substituted at the nitrogen atom of its 4-position by $C_{1-4}$ alkyl, phenyl-$C_{1-4}$ alkyl or $C_{2-4}$ alkanoyl, or two of $R^1$, $R^2$, $R^3$ and $R^4$ together form —CH=CH—CH=CH— at adjacent carbon atoms of the benzene ring, and a pharmaceutically acceptable carrier or diluent therefor.

16. A pharmaceutical composition for managing peptic ulcer which comprises, as an active ingredient, an effective amount of a compound of the formula

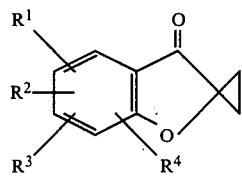

wherein
each of $R^1$, $R^2$, $R^3$ and $R^4$ independently hydrogen, $C_{1-6}$ alkyl, nitro, halogen, hydroxyl, $C_{1-6}$ alkoxy, mono- or di-$C_{1-4}$ alkylamino-$C_{1-6}$ alkoxy, phenyl-$C_{1-4}$ alkyloxy, $C_{2-6}$ alkanoyloxy, benzoyloxy, $C_{2-6}$ alkanoyl, benzoyl, sulfamoyl, amino, $C_{1-4}$ alkylamino, di-$C_{1-4}$ alkylamino, $C_{2-4}$ alkanoylamino, $C_{1-4}$ alkanesulfonylamino, 1-pyrrolidinyl, piperidino, a 1-piperazinyl group, or morpholino, said 1-piperazinyl group being unsubstituted or substituted at the nitrogen atom of its 4-position by $C_{1-4}$ alkyl, phenyl-$C_{1-4}$ alkyl or $C_{2-4}$ alkanoyl, or two of $R^1$, $R^2$, $R^3$ and $R^4$ together form —CH=CH—CH=CH— at adjacent carbon atoms of the benzene ring and a pharmaceutically acceptable carrier or diluent therefor.

17. A method of managing peptic ulcer in a patient which comprises administering to said patient a compound of the formula

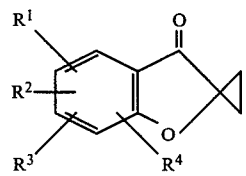

wherein
each of $R^1$, $R^2$, $R^3$ and $R^4$ is independently hydrogen, $C_{1-6}$ alkyl, nitro, halogen, hydroxyl, $C_{1-6}$ alkoxy, mono- or di-$C_{1-4}$ alkylamino-$C_{1-6}$ alkoxy, phenyl-$C_{1-4}$ alkyloxy, $C_{2-6}$ alkanoyloxy, benzoyloxy, $C_{2-6}$ alkanoyl, benzoyl, sulfamoyl, carboxyl, $C_{2-6}$ alkoxycarbonyl, carbamoyl, $C_{1-4}$ alkylcarbamoyl, di-$C_{1-4}$ alkylamino-$C_{1-4}$ alkylcarbamoyl, N-$C_{1-4}$ alkylpyrrolidinyl-$C_{1-4}$ alkylcarbamoyl, ureido, $C_{1-4}$ alkylureido, thioureido, $C_{1-4}$ alkylthioureido, $C_{1-4}$ alkylthio, $C_{1-4}$ alkylsulfinyl, $C_{1-4}$ alkylsulfonyl, aminomethyl, mono- or di-$C_{1-4}$ alkylaminomethyl, cyano, phenyl, amino, mono- or bis-($\beta$-hydroxyethyl)amino, $C_{1-4}$ alkylamino, di-$C_{1-4}$ alkylamino, $C_{2-4}$ alkanoylamino, $C_{1-4}$ alkanesulfonylamino, 1-pyrrolidinyl, piperidino, a 1-piperazinyl group, or morpholino, said 1-piperazinyl group being unsubstituted or substituted at the nitrogen atoms of its 4-position by $C_{1-4}$ alkyl, phenyl-$C_{1-4}$ alkyl or $C_{2-4}$ alkanoyl, or two of $R^1$, $R^2$, $R^3$ and $R^4$ together form —CH=CH—CH=CH— at adjacent carbon atoms of the benzene ring.

said compound being administered in an amount effective to manage peptic ulcer in said patient.

18. A method of managing peptic ulcer in a patient which comprises administering to said patient a compound of the formula

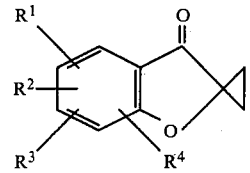

wherein
each of $R^1$, $R^2$, $R^3$ and $R^4$ is independently hydrogen, $C_{1-6}$ alkyl, nitro, halogen, hydroxyl, $C_{1-6}$ alkoxy, mono- or di-$C_{1-4}$ alkylamino-$C_{1-6}$ alkoxy, phenyl-$C_{1-4}$ alkyloxy, $C_{2-6}$ alkanoyloxy, benzoyloxy, $C_{2-6}$ alkanoyl, benzoyl, sulfamoyl, amino, $C_{1-4}$ alkylamino, di-$C_{1-4}$ alkylamino, $C_{2-4}$ alkanoylamino, $C_{1-4}$ alkanesulfonylamino, 1-pyrrolidinyl, piperidino, a 1-piperazinyl group, or morpholino, said 1-piperazinyl group being unsubstituted or substituted at the nitrogen atom of its 4-position by $C_{1-4}$ alkyl, phenyl-$C_{1-4}$ alkyl or $C_{2-4}$ alkanoyl, or two of $R^1$, $R^2$, $R^3$ and $R^4$ together form —CH=CH—CH=CH— at adjacent carbon atoms of the benzene ring, said compound being administered in an amount effective to manage peptic ulcer in said patient.

19. A method according to claim 18, wherein $R^1$ is di-$C_{1-4}$ alkylamino and $R^2$, $R^3$ and $R^4$ are hydrogen.

20. A method according to claim 18, wherein $R^1$ is $C_{2-6}$ alkanoyl and $R^2$, $R^3$ and $R^4$ are hydrogen.

21. The method according to claim 18, wherein the compound is spiro[benzo[b]furan-2(3H),1'-cyclopropane]-3-one.

22. The method according to claim 18, wherein the compound is spiro[naphtho[2,3-b]furan-2(3H),1'-cyclopropane]-3-one.

23. The method according to claim 18, wherein the compound is 5-nitrospiro[benzo[b]furan-2(3H),1'-cyclopropane]-3-one.

24. The method according to claim 18, wherein the compound is 5-aminospiro[benzo[b]furan-2(3H),1'-cyclopropane]-3-one.

25. The method according to claim 18, wherein the compound is 5-methylaminospiro[benzo[b]furan-2(3H),1'-cyclopropane]-3-one.

26. A method of managing peptic ulcer in a patient which comprises administering to said patient a compound of the formula

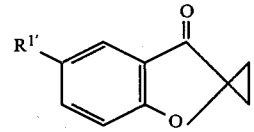

wherein $R^{1'}$ is di-$C_{1-4}$ alkylamino, or a pharmaceutically acceptable salt thereof, said compound or salt being administered in an amount effective to manage peptic ulcer in said patient.

27. The method according to claim 26, wherein the compound is 5-dimethylaminospiro[benzo[b]furan-2(3H),1'-cyclopropane]-3-one.

28. The method according to claim 26, wherein the compound is 5-diethylaminospiro[benzo[b]furan-2(3H),1'-cyclopropane]-3-one.

29. A method of managing peptic ulcer in a patient which comprises administering to said patient a compound of the formula

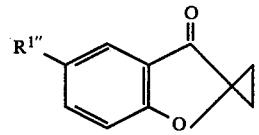

wherein R¹'' is $C_{2-6}$ alkanoyl, said compound being administered in an amount effective to manage peptic ulcer in said patient.

30. The method according to claim 29, wherein the compound is 5-acetylspiro[benzo[b]furan-2(3H),1'-cyclopropane]-3-one.

* * * * *